US012614623B2

(12) United States Patent (10) Patent No.: US 12,614,623 B2
Craig (45) Date of Patent: Apr. 28, 2026

(54) PLANNING AND NAVIGATION IN SUPERSELECTIVE DRUG DELIVERY VIA THE TRACHEOBRONCHIAL AIRWAY

(71) Applicant: ISOLA THERAPEUTICS, INC., Minneapolis, MN (US)

(72) Inventor: Brian H. Craig, Minneapolis, MN (US)

(73) Assignee: ISOLA THERAPEUTICS, INC., Minneapolis, MN (US)

( * ) Notice: Subject to any disclaimer, the term of this patent is extended or adjusted under 35 U.S.C. 154(b) by 124 days.

(21) Appl. No.: 17/785,647

(22) PCT Filed: Dec. 18, 2020

(86) PCT No.: PCT/US2020/065986
§ 371 (c)(1),
(2) Date: Jun. 15, 2022

(87) PCT Pub. No.: WO2021/127416
PCT Pub. Date: Jun. 24, 2021

(65) Prior Publication Data
US 2023/0049856 A1    Feb. 16, 2023

Related U.S. Application Data

(60) Provisional application No. 62/951,463, filed on Dec. 20, 2019.

(51) Int. Cl.
*G16H 20/40*        (2018.01)
*G16H 30/40*        (2018.01)

(52) U.S. Cl.
CPC ............. *G16H 20/40* (2018.01); *G16H 30/40* (2018.01)

(58) Field of Classification Search
CPC ........ G16H 20/40; G16H 30/40; G16H 20/10; A61B 6/5217; A61B 6/032; A61B 6/037;
(Continued)

(56) References Cited

U.S. PATENT DOCUMENTS 10,089,413 B2 * 10/2018 Wirx-Speetjens ..... B33Y 50/00
2012/0136343 A1 * 5/2012 Burnett .................. A61B 18/04
606/27

(Continued)

FOREIGN PATENT DOCUMENTS

EP        3409234 A1    12/2018
WO    2019099036 A1    5/2019

OTHER PUBLICATIONS

Mark E. Gray, A Novel Translational Ovine Pulmonary Adenocarcinoma Model for Human Lung Cancer, Jun. 18, 2019, Frontiers in Oncology, Sec. Molecular and Cellular Oncology, vol. 9—2019 | https://doi.org/10.3389/fonc.2019.00534 (Year: 2019).*

(Continued)

*Primary Examiner* — Stella Higgs
(74) *Attorney, Agent, or Firm* — MEDLER FERRO WOODHOUSE & MILLS PLLC

(57)        ABSTRACT

Devices, systems, and methods for localized delivery of a chemotherapy, hormonal therapy, or targeted drug/biologic therapy to a target tissue area of an internal body organ of a patient. Computer systems may be used for planning and navigation in super selective drug delivery via a tracheobronchial airway. A catheter may be used to form a sealed treatment chamber in a natural lumen extending through the target tissue area. Air is purged from the chamber, which is then filled with a liquid drug solution for an adequate treatment session time, solution volume and drug concentration to saturate the target tissue area, thereby providing the treatment. The liquid drug solution may be circulated or recirculated through the chamber or maintained stationary therewithin to saturate the target tissue area. The chamber is evacuated at the end of the treatment session.

13 Claims, 14 Drawing Sheets

(58) Field of Classification Search
CPC ........... A61B 6/50; A61B 2017/00026; A61B
2034/2048; A61B 2034/2051; A61B
2090/3735; A61B 2090/376; A61B
2090/3966; A61B 34/20; A61B 34/10
See application file for complete search history.

(56) References Cited

U.S. PATENT DOCUMENTS

| | | | |
|---|---|---|---|
| 2016/0038247 A1* | 2/2016 | Bharadwaj ............. | A61B 34/10 |
| | | | 600/426 |
| 2016/0271379 A1* | 9/2016 | Pouliot .................. | A61B 6/037 |
| 2018/0110964 A1* | 4/2018 | Weadock ................. | A61N 5/02 |
| 2018/0200385 A1 | 7/2018 | Malik et al. | |
| 2019/0231287 A1* | 8/2019 | Krimsky ............... | A61B 8/466 |
| 2019/0269933 A1 | 9/2019 | Kaplan et al. | |
| 2019/0371450 A1 | 12/2019 | Lou et al. | |

OTHER PUBLICATIONS

International Search Report issued Mar. 24, 2021 in Int'l Appl. No.
PCT/US2020/065986.
Extended European Search Report issued Nov. 20, 2023 in EP Appl.
No. 20 904 104.5.
Communication pursuant to Article 94(3) EPC dated Aug. 13, 2024
in EP Appl. No. 20 904 104.5.

\* cited by examiner

*102*

Processor
*110*

Digital Map Manager *251*

Treatment Zone Manager *252*

Treatment Plan Manager *253*

Navigation Manager *254*

User Interface Manager *255*

Data Manager *256*

Storage Device *120*

*1900*

*1902* Accessing Image Data

*1904* Creating digital map

*1906* Defining tumor treatment zones

*1908* Generating treatment plan

PLANNING AND NAVIGATION IN SUPERSELECTIVE DRUG DELIVERY VIA THE TRACHEOBRONCHIAL AIRWAY

TECHNICAL FIELD

The present disclosure relates to methods for delivery of a drug to a target tissue area of an internal body organ of a patient and, more particularly, relates to intraluminal catheters and methods for generating and executing treatment plans to treat cancer and other diseases by localized chemotherapy, hormonal therapy, or targeted drug/biologic therapy.

BACKGROUND

Many chemotherapeutics are systemic, which creates the limitations as described in the following paragraphs.

Toxicity: Systemic toxicity can create issues that result in restricting therapeutic dosing and are associated with a range of adverse effects that are either life threatening, e.g. immunosuppression, neutropenic enterocolitis, gastrointestinal distress, tumor lysis syndrome, organ damage, or are lifestyle limiting, e.g. anemia, fatigue, nausea/vomiting, hair loss, infertility, teratogenicity, peripheral neuropathy, cognitive impairment, potentially making chemotherapy dangerous or at least stressful to the body.

Repeat Dosing: Most chemotherapeutics are delivered intravenously (IV) but some may be delivered orally, which requires they must be prepared in a way that allows the drug to survive stomach acid while being able to be absorbed in the intestines. Many require multiple doses, which require ongoing risk to potential adverse events and patient compliance to dosing regimens.

SUMMARY

An embodiment includes a computer-implemented method for generating a tumor treatment, the method being implemented by at least one processing unit programmed with computer program instructions that, when executed, cause the at least one processing unit to perform the method. The method including accessing image data acquired by non-invasive imaging of a lower respiratory tract of a patient, creating a digital map identifying one or more lung cancer tumors and one or more respiratory airways proximate to the one or more lung cancer tumors according to the image data, defining, according to an analysis of the digital map, one or more tumor treatment zones for permeation of a drug into lung tissue surrounding portions of one or more respiratory airways, wherein the one or more tumor treatment zones are distal of defined treatment positions of the one or more respiratory airways, and generating a treatment plan according to the one or more tumor treatment zones.

An additional embodiment includes a non-transitory computer-readable medium having instructions stored thereon that, when executed by at least one processing unit, cause the at least one processing unit to: access image data acquired by non-invasive imaging of a lower respiratory tract of a patient; create, according to the image data, a digital map identifying one or more lung cancer tumors and one or more respiratory airways proximate to the one or more lung cancer tumors; define, according to an analysis of the digital map, one or more tumor treatment zones for permeation of a drug into lung tissue surrounding portions of the one or more respiratory airways, wherein the one or more tumor treatment zones are distal of defined treatment positions of the one or more respiratory airways; and generate a treatment plan according to the one or more tumor treatment zones.

An additional embodiment includes a system having at least one memory unit, and at least one processing unit programmed according to instructions on the at least one memory unit. The at least one processing unit being configured to: access image data acquired by non-invasive imaging of a lower respiratory tract of a patient; create, according to the image data, a digital map identifying one or more lung cancer tumors and one or more respiratory airways proximate to the one or more lung cancer tumors; define, according to an analysis of the digital map, one or more tumor treatment zones for permeation of a drug into lung tissue surrounding portions of the one or more respiratory airways, wherein the one or more tumor treatment zones are distal of defined treatment positions of the one or more respiratory airways; and generate a treatment plan according to the one or more tumor treatment zones.

BRIEF DESCRIPTION OF THE DRAWINGS

The drawings are not necessarily to scale. Like numbers used in the figures refer to like components, steps, and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Specific embodiments of the present technology are now described with reference to the figures, wherein like reference numbers indicate identical or functionally similar elements. The terms "distal" and "proximal" are used in the following description with respect to a position or direction relative to the treating operator. "Distal" or "distally" are a position distant from or in a direction away from the operator. "Proximal" and "proximally" are a position near or in a direction toward the operator. The term "target," as in "target tissue, target area, target organ, or target region" is used to refer to diseased tissue of a hollow organ and/or tissue of a natural tract or lumen extending therethrough.

The following detailed description is merely exemplary in nature and is not intended to limit the scope of the present technology or the application and uses of the present technology. Platforms and methods of this disclosure may reduce the limitations of systemic drug delivery. A highly localized method of chemotherapy may reduce complications and increase effectiveness for inductive (curative), neoadjuvant (prior to surgery), or adjuvant (after surgery) drug treatments. Such a treatment may be localized to hollow organ or natural lumens. A selected drug can be delivered in liquid, aerosol/nebulizer, or even sprayed. The hollow organ is locally bathed in the drug to achieve drug absorption into the targeted organ tissue. Although the description of embodiments hereof is in the context of treatments performed within a variety of natural hollow body lumens or tracts, the present technology may also be used in any other body passageways or in extraluminal locations where it is deemed useful. Furthermore, there is no intention to be bound by any expressed or implied theory presented in the preceding technical field, background, brief summary or the following detailed description.

Figure 1:
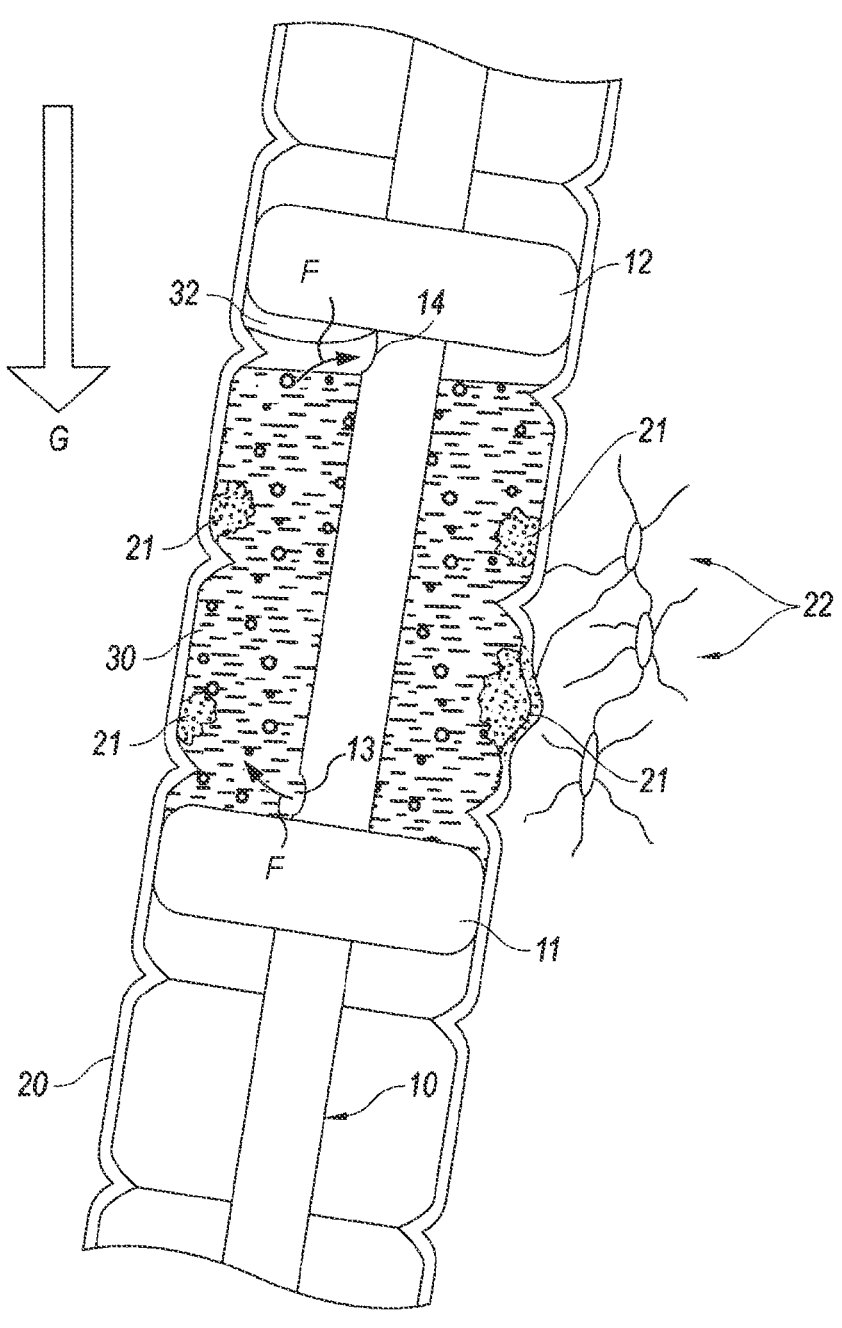
FIG. 1 illustrates a chemotherapeutic treatment of a portion of an intestine using a catheter in accordance with an embodiment of the disclosure.
Figure 6:
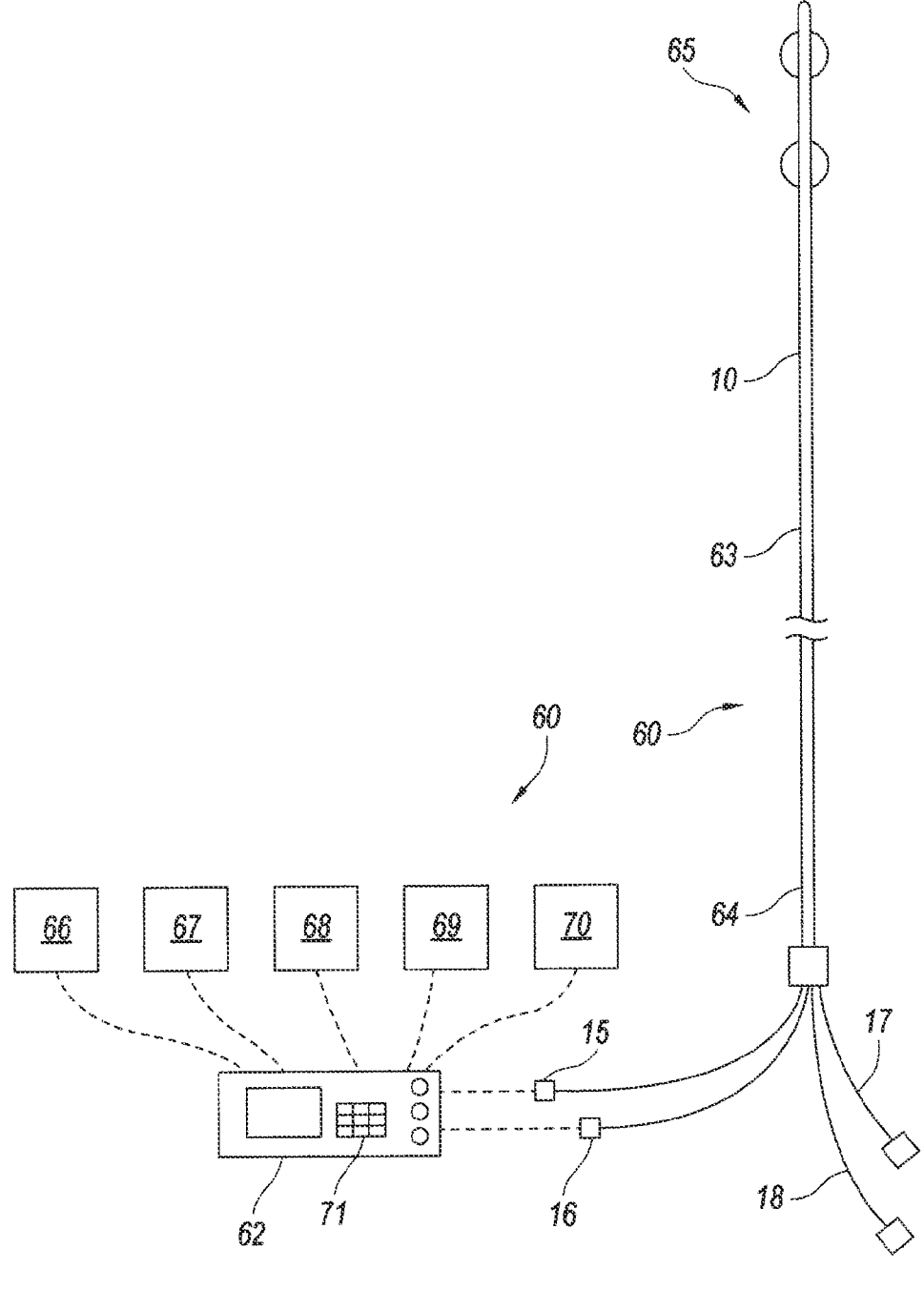
FIG. 6 is a schematic view of a treatment system in accordance with the disclosure.

FIG. 1 illustrates a catheter 10 configured in accordance with an embodiment of the present technology. The catheter 10 having an elongate flexible shaft is shown in a deployed configuration within a target region of a natural lumen, which in this example is a portion of a large intestine or the colon 20. Expandable members 11, 12 are mounted about a distal region of the catheter 10, and are longitudinally spaced apart such that, when expanded into sealing contact with the inner wall of the colon 20, a closed treatment chamber is defined between the expandable members 11, 12 and the intestinal wall. The treatment chamber may be considered to be an annular chamber because of the annular cylinder formed between the catheter shaft and the natural lumen. Herein, "closed" means that the treatment chamber is excluded from fluid communication with other parts of the natural lumen beyond the expandable members. An expandable member for the present technology may be a mechanically operated sealing element or a balloon that is inflatable with a fluid that may be either a gas or a liquid. In the illustrated embodiment, the treatment chamber includes one or more polyps or other cancers 21. The catheter 10 is reversible, meaning that the flexible catheter shaft may be considered to extend proximally either upward or downward in FIG. 1. The ports 13, 14 fluidly communicate the treatment chamber with respective lumens (not shown) that extend proximally through the catheter to terminate at respective fluid connectors 15, 16 located at the proximal end thereof, as shown in FIG. 6.

Figure 4:
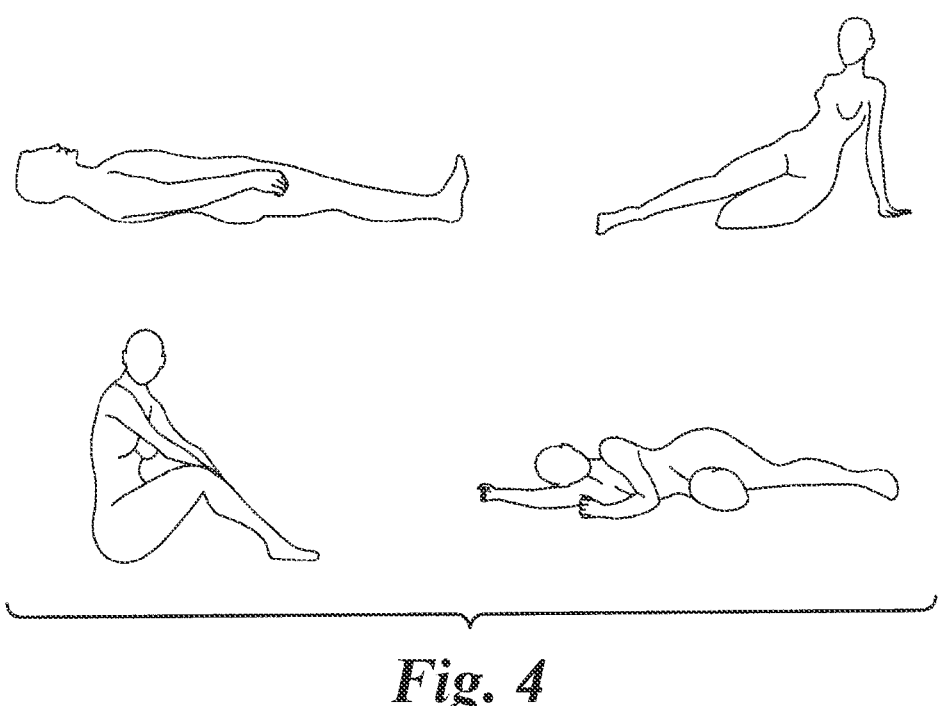
FIG. 4 shows several exemplary positions a patient may assume during a treatment procedure in accordance with the disclosure.

Once the catheter 10 has been deployed as shown in FIG. 1, the operator may assess the orientation of the treatment chamber with respect to gravity G, and may reposition the patient, if necessary, to orient the treatment chamber as close to vertical as possible to facilitate air evacuation as the chamber is filled with liquid. The avoidance of air bubbles or air pockets may ensure that all of the inner wall of the colon 20 in the treatment chamber is bathed in liquid drug solution 30. FIG. 4 shows examples of different patient positions that may provide a vertical treatment chamber. In the embodiment illustrated in FIG. 1, the portion of the colon 20 enclosing the treatment chamber is nearly vertical with the port 14 being located at a high point in the chamber. Because the catheter 10 is reversible, the patient or the catheter could be positioned such that the port 13 is located at a high point in the chamber (not shown). It is the operator's choice how to position or repositioning the patient, based on comfort of the patient and convenience of the operator and as a result, either of the ports 13, 14 may become the upper port in the treatment chamber. The upper port may be defined as the egress port and the other, lower port may then be defined as the ingress port. Once the treatment chamber, catheter lumens, extension lines (if used), and pump are purged of air as described below, the patient may be repositioned or returned to a position that may be more comfortable for the patient and/or more convenient for the operator.

After the treatment chamber is oriented with respect to gravity, a liquid drug solution 30 is admitted or pumped into the chamber via the ingress port, i.e. port 13 in FIG. 1. As the liquid drug solution 30 fills the treatment chamber from bottom to top, air is purged from the chamber via the egress port, i.e., the port 14 until the liquid drug solution reaches the port 14, as illustrated by the flow arrows F in FIG. 1. Optionally, partial vacuum may be applied to egress port 14 (the upper part) to assist or hasten the purging process. In this way, the treatment chamber is filled with the liquid drug solution 30, leaving only a small air bubble 32, or preferably no air bubble at all. After the treatment chamber is filled with the liquid drug solution 30, air may also be purged from all catheter lumens, extension lines (if used), and a circulating pump such as the pump 67 described below to form a closed fluid circuit that may be a closed-loop fluid circuit.

In another purging method, after the treatment chamber is oriented with respect to gravity, a liquid such as sterile saline is pushed into the chamber via the ingress port, i.e., the port 13 in FIG. 1. As saline fills the treatment chamber from bottom to top, air is purged from the chamber via the egress port, i.e., the port 14 until the saline reaches port 14. See flow arrows F in FIG. 1. After the treatment chamber is filled with saline, air may also be purged from all catheter lumens, extension lines (if used), and a circulating pump such as pump 67 described below to form a closed fluid circuit that may be a closed-loop fluid circuit. The saline in the fluid circuit can then be replaced with the liquid drug solution 30.

Once the closed fluid circuit is purged of air and filled with the liquid drug solution 30, a treatment session may then be conducted by circulating the liquid drug through the closed fluid circuit to maintain a homogeneous concentration of the drug throughout the treatment chamber. Herein, "circulating" means causing a fixed volume of the liquid drug solution 30 to flow through the closed fluid circuit between first and second external reservoirs, e.g. first and second syringes connected to the respective fluid connectors 15, 16 shown in FIG. 6, without intentional loss of the liquid solution either inside or outside of the patient. The circulating flow of the liquid drug solution 30 may be unidirectional during the treatment session or may reverse direction one or more times between the first and second reservoirs. Pushing or filling a liquid, either a drug solution or saline, from a first graduated syringe through the closed fluid circuit and into a second graduated syringe allows the operator to initially confirm and subsequently monitor seal integrity of the treatment chamber by comparing input and output volumes.

Alternatively, the fluid connectors 15, 16 may be connected to input and output ports of a pump thereby forming a closed-loop fluid circuit. Herein, a "closed-loop fluid circuit" is considered to be a subset of closed fluid circuits. In this arrangement, a treatment session may be conducted by recirculating the liquid drug solution 30 through the closed-loop fluid circuit to maintain a homogeneous concentration of the drug throughout the treatment chamber. Herein, "recirculating" is considered to be a subset of "circulating," and means causing the liquid drug solution 30 to continuously flow, e.g. via the pump 67 shown in FIG. 6 through a closed-loop fluid circuit without intentional loss of the liquid solution either inside or outside of the patient.

To conduct chemotherapy safely and effectively in accordance with an embodiment of the present technology, it may be useful to predetermine a desired dose of drug to permeate or be dispensed or absorbed into the target tissue, and to measure, monitor, calculate or otherwise estimate attainment or progress towards that pharmacokinetic goal during or at the end of a treatment session. To predetermine the desired dose, it may be useful to estimate the volume of tissue targeted for saturation with the drug molecules from the liquid drug solution 30. Target tissue volume may be estimated based on the surface area of the tissue comprising the treatment chamber in a given patient. To predetermine the desired dose, it may also be useful to know or estimate the rate of transfer of the drug through the wall of the natural lumen and into the target tissue area.

One parameter that may be used to calculate the exposed tissue surface area may be the liquid capacity of the treatment chamber as measured by the volume of liquid pumped into the fluid circuit during the air purging step. For example, the liquid drug solution 30 or sterile saline may be admitted by a graduated syringe to the ingress port via one of the fluid connectors 15 or 16 shown in FIG. 6, and the volume of the admitted liquid drug solution 30 is measured when the liquid begins to appear at the other of the fluid connectors 15 or 16 in fluid communication with the purge port. Other parameters that may be used to calculate the exposed tissue surface area may be a known distance between the pair of expandable members, a diameter of at least one of the expandable members, a distance from the natural orifice of the natural lumen to the two or more expandable members, an analysis of current and/or previous medical images of the natural lumen extending through the target tissue area of the internal body organ of the patient, and a statistical analysis of historical data regarding physical dimensions of similar natural lumens extending through similar target tissue areas for a known population of patients. The diameter of at least one of the expandable members may be measured from a medical image or the expandable member may be an inflatable elastic balloon and a diameter of the balloon is determined based at least in part on a volume of a fluid or air used to inflate the balloon into sealing contact with the inner wall of the natural lumen.

A treatment session may be terminated when the desired drug dose has been delivered to the target tissue. The amount of drug delivered via the treatment chamber may be estimated using parameters including the volume of the closed-loop fluid circuit, the volume of the target tissue, and the change in concentration of the drug in recirculating the liquid drug solution 30. Thus, the amount of drug calculated as missing from the volume of liquid in the closed-loop fluid circuit is presumed to have permeated into the target tissue.

An alternative method of estimating the amount of drug delivered during a treatment session may be based on elapsed time and parameters such as a known permeability rate for a given concentration of drug in a given tissue type. Such parameters may be drawn from data regarding a general population rather than requiring data from the current patient. In this method, the size of the surface area of target tissue may or may not be useful to determine whether the desired drug dose has been delivered to the target tissue.

Another method in accordance with an embodiment of the present technology may involve continuing to recirculate the liquid drug solution 30 through the closed-loop fluid circuit beyond the point of saturating the target tissue with a selected anti-cancer drug. The drug may permeate the target tissue, enter, and activate the lymphatic system 22 or interstitial space, all of which may act as a conduit or reservoir for the drug to continue eluting drug into cancerous tissue after the session has been terminated and the catheter is removed from the patient.

Another method in accordance with an embodiment of the present technology is to fill the treatment chamber with the liquid drug solution 30 of a known, e.g., calculated drug concentration for a selected period of time without circulation or recirculation. That is, the liquid drug solution 30 carries a measured amount of the drug and remains stationary in the treatment chamber for a duration that is expected to achieve the desired drug dosing.

Alternatively, a treatment session may be terminated when an amount of drug measured in the patient's blood reaches a predetermined level, which may be selected to be a level indicating that the desired drug dosage has been delivered to the target tissue. A predetermined threshold of drug concentration in the blood may also be set such that drug concentration in the blood above that level may be considered to be approaching a toxic condition. The amount of drug detected in the patient's bloodstream may indicate that the selected anti-cancer drug has been absorbed from the non-vascular natural hollow body lumen, has saturated the target tissue, and has begun entering the vasculature.

Measuring drug concentration in a patient's blood during treatment may be a particularly sensitive and useful monitoring technique in treatments where the target tissue is highly vascularized, for example in the lungs. Monitoring of a patient's blood serum drug level may be done by intermittent blood sampling, e.g. via a venipuncture or an indwelling arterial or central venous line. Alternatively, blood serum drug level may be monitored continuously in real time by circulating the patient's blood through a measuring device such as the console 62 below, and associated components similar to the pump 67 and an osmometer 68. In such an arrangement, the console 62 can notify a clinician and/or terminate treatment if an amount of drug measured in the patient's blood reaches a predetermined level.

When the desired drug dosing has been achieved and the treatment session is terminated, the treatment chamber may be evacuated by pumping a flushing fluid therethrough, in similar fashion to the air purging step described above. A non-toxic flushing fluid such as air, saline, or other gases or liquids may be used to clear liquid drug solution 30 from the treatment chamber, leaving the flushing fluid therein. Clearing the anti-cancer drug from the treatment chamber may prevent target tissue from being exposed to the drug for a longer time than desired, and/or may prevent non-target tissue from being exposed to the drug when the treatment chamber is broken down by returning the expandable members 11, 12 to the collapsed delivery configuration to permit removal of the catheter 10 from the patient.

Figure 2:
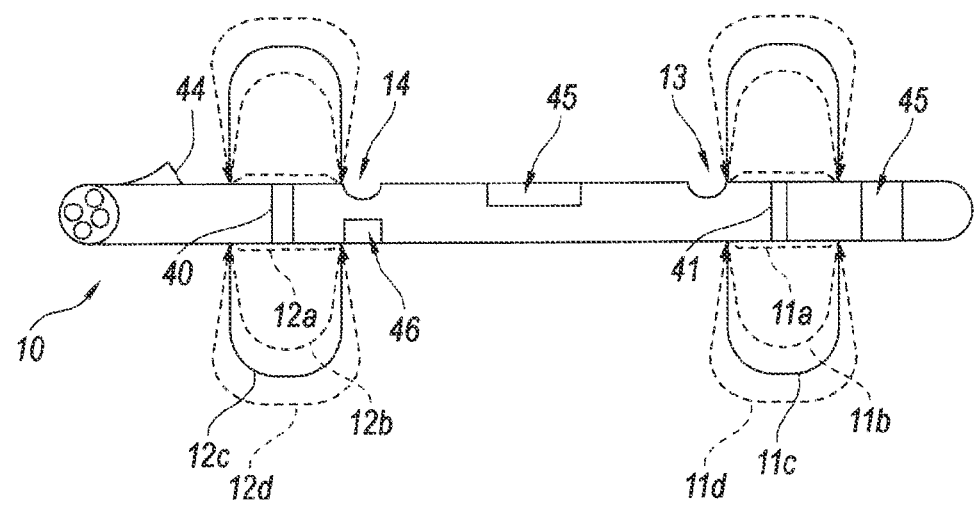
FIG. 2 shows a distal portion of a catheter in accordance with another embodiment of the disclosure.
Figure 3:
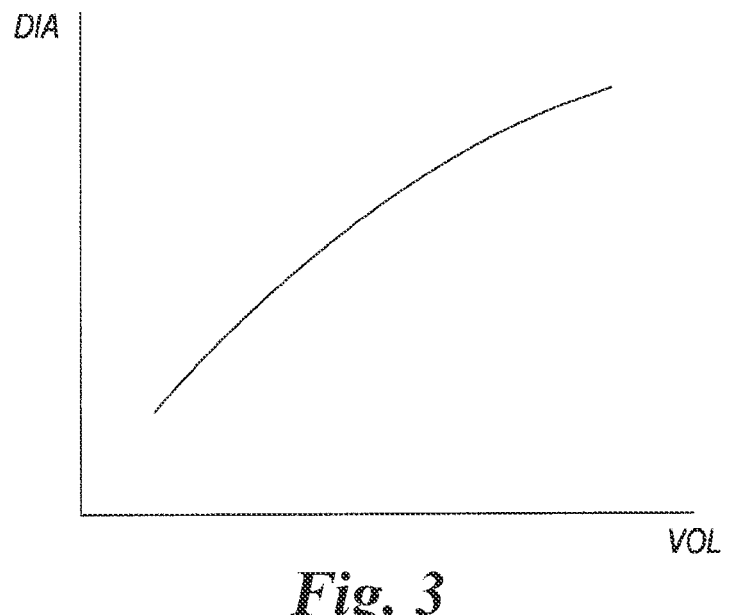
FIG. 3 is a graph of an exemplary known relationship of diameter to inflation volume for a sealing balloon in accordance with the disclosure.

FIG. 2 illustrates a distal region of another catheter 10 configured in accordance with an embodiment of the present technology. Expandable members 11, 12 are shown with variable diameters including fully collapsed respective configurations 11*a*, 12*a*, and increasingly larger configurations 11*b*, 12*b*; 11*c*, 12*c*; and 11*d*, 12*d*. The variability in diameter of the expandable members 11, 12 allows each member to be selectively expanded into sealing engagement with a natural lumen such as the colon illustrated in FIG. 1. The expandable members 11, 12 may be inflatable elastic balloons, wherein each balloon has a diameter that corresponds in a known relationship to either a gas pressure or a liquid volume, as illustrated in FIG. 3. The selected balloon may be characterized as compliant, non-compliant, elastic, or inelastic, depending on its diameter-to-volume or diameter-to-pressure properties. In an example, a catheter having an inelastic balloon may be selected in cases where the known inflated diameter of the balloon can be expected to create an effective treatment chamber seal at the intended anatomic location. In the case of the expandable members 11, 12 comprising two balloons, the balloons may be inflated together or separately, to the same or different diameters, and via common or separate inflation lumens 17, 18 shown in FIG. 6, as would be known to those of skill in the field of balloon catheters. Ports 13, 14 are illustrated as being positioned as close to the expandable members 11, 12 as possible. The shape of the expandable members 11, 12 and the adjacent location of the ports thereto can be selected to optimize purging of air from the treatment chamber. For example, a balloon may be mounted to the catheter 10 with an inverted neck (not shown) to permit locating a port closer to the expandable body of the balloon. Additionally, or alternatively, the expandable members 11, 12 may have a concave or invaginated surface facing towards the treatment chamber to enhance air purging by directing air away from the lumen wall and towards the egress port in the catheter shaft.

The embodiment of the catheter 10 shown in FIG. 2 has the following optional features. Fiducial markers 40, 41 may be associated with the expandable members 11, 12. To assist in locating the treatment chamber with respect to a target area, the markers 40, 41 may be visible under medical imaging, e.g. radiopaque markers for visualization under fluoroscopy or sensors (like electromagnetic coils) for use in navigation systems. An orientation sensor 43 may be located proximate the distal region of the catheter 10 to inform the operator of the angle of the catheter 10 with respect to gravity. The axis of the distal region of the catheter 10 is expected to be generally coaxial with the treatment chamber due to the centering effect of the expandable members 11, 12. The orientation sensor 43 may be an accelerometer adapted to communicate with an electronic console exterior to the patient.

The orientation sensor 43 may alternatively be an inertial measurement unit (IMU), which is an electronic device that measures and reports an object's specific acceleration, angular rate, and magnetic field surrounding the object, using a combination of accelerometers, gyroscopes, and magnetometers. An IMU works by detecting linear acceleration, rotational rate, and heading reference. When applied to each axis, an IMU can provide pitch, roll, and yaw as well as linear movement. When incorporated into Inertial Navigation Systems, the raw IMU measurement data are utilized to calculate attitude, angular rates, linear velocity, and position relative to a global reference frame. IMU data allows a computer to track an object's position, using a method known as dead reckoning or the process of calculating one's current position by using a previously determined position, or fix, and advancing that position based upon known or estimated speeds over elapsed time and course. IMU navigation can suffer accuracy limitations from accumulated error or drift. This error is expected to be reduced in the present technology by combining IMU data with image data generated by a camera 44 such that each subsequent image serves as both a new and a cumulative navigational reference. Associating each image frame or a sampling of image frames with a discrete distal IMU pose data point to create a discrete image pose datum is expected to allow navigation errors to be removed.

The camera 44 may be located proximate the distal region of the catheter 10 to assist in locating the treatment chamber with respect to a target area. The camera may use optical coherence tomography (OCT) or other small medical camera technologies. A pressure sensor 45 may be located between the expandable members 11, 12 to provide data regarding fluid pressure within the treatment chamber. The pressure sensor 45 may utilize the piezoelectric effect or other technologies, with the pressure data being useful to monitor and/or maintain safe and effective pressure within the treatment chamber and to potentially detect leakage from the chamber. One or more electrodes 46 may be located between the expandable members and positioned as close as possible thereto. The electrode 46 may be used to monitor electrical impedance, which may be useful to detect when the treatment chamber has filled with liquid or monitor changes in drug concentration.

Figure 5:
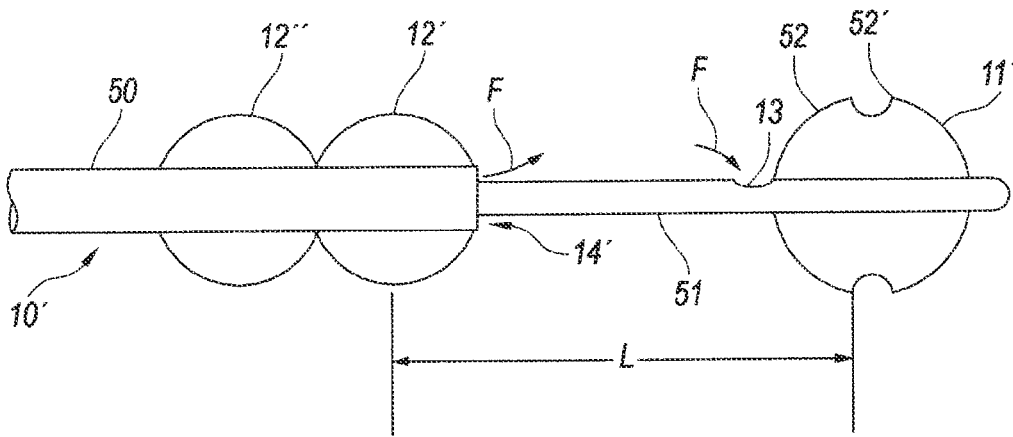
FIG. 5 shows a distal portion of a catheter in accordance with another embodiment of the disclosure.

The embodiment of a catheter 10' shown in FIG. 5 has the following optional features. The catheter 10' comprises a first catheter shaft 50 having an expandable member 12' mounted at the distal end thereof. A second catheter shaft 51 is slidably disposed within a lumen through the shaft 50 and extends distally therefrom. An expandable member 11' is mounted about a distal region of the shaft 51. The operator may adjust how much of the shaft 51 extends from the shaft 50 to selectively define the length L of the treatment chamber formable between the expandable members 11', 12'. A port 14' may be an annular clearance space at the terminus of the lumen in the shaft 50 that slidably receives the shaft 51. The ports 13 and 14' may function as shown in previous embodiments, including their reversibility, as described above.

The catheter 10' also comprises a second expandable member 12" mounted adjacent the expandable member 12' to provide additional sealing capability against a luminal wall beyond that provided by the expandable member 12' alone. This additional, adjacent balloon may serve as a redundant safety feature should sealing of one of the balloons fail. Additional sensors (electrodes, cameras, pressure monitors, etc.) may be placed between these balloons to monitor for fluids indicating a failed seal. The expandable member 11' comprises multiple lobes 52, 52' that may also provide additional sealing capability against a luminal wall. A plurality of expandable members, balloons, or lobes may thus be provided to form one or both ends of a treatment chamber in accordance with embodiments of the present technology.

FIG. 6 illustrates a drug delivery system 60 configured in accordance with an embodiment of the present technology. The system 60 includes the catheters 10 or 10' operably coupled to a console 62. Alternatively, the system 60 may include other catheters in accordance with the present technology, such as catheters 710, 810 described below. The catheter 10 as illustrated in FIG. 6 includes selected features of the catheter embodiments described above, and further includes a flexible elongate shaft 63, a proximal portion 64, and a distal portion 65. Fluid connectors 15, 16 are in fluid communication with ports 13, 14 at a distal region 65 and may be attached directly or via extension tubes (shown in broken lines) to the console 62. Inflation lumens 17, 18 are in fluid communication with expandable members at the distal region 65 and may be in communication with separate inflation devices (not shown) or may be connected to the console 62 in an embodiment where inflation devices are incorporated therein.

The console 62 may incorporate or be operably coupled to several components adapted to serve different functions as follows. A reservoir 66 may contain liquid drug solution 30; a pump 67 may recirculate the liquid drug solution 30 via the catheter fluid connectors 15, 16; and an osmometer 68 may monitor the concentration of the drug in the recirculating liquid drug solution 30. A pressure sensor 69 may electronically communicate with the pressure sensor 45 shown in FIG. 2 or may directly measure pressure in the recirculating liquid drug solution 30 within the console 62. A control unit 70 may operate the pump 67 based at least in part on one or more inputs selected from elapsed time, instantaneous pressure in the closed-loop recirculating fluid circuit, amount of the liquid drug solution 30 added to the fluid circuit, instantaneous drug concentration of the liquid drug solution 30 occupying the closed-loop recirculating fluid circuit, and manual data entered by an operator, e.g. by a keypad 71 on the console 62. The pressure in the closed-loop recirculating fluid circuit may be established, maintained, and changed by the pump 67. For example, the pump 67 may provide a partial vacuum, a.k.a. negative pressure to the egress lumen and egress port to help evacuate the treatment chamber in preparation for administering the liquid drug solution 30 at the beginning of a treatment session or for clearing the treatment chamber of the liquid drug solution 30 at the end of a treatment session. The pump 67 may also maintain pressure of the liquid drug solution 30 in the treatment chamber at a selected elevated level, e.g. above atmospheric pressure, or above patient blood pressure, to enhance or facilitate uptake of the drug into the target tissue while limiting the selected pressure to avoid injury to tissue or leakage of the liquid drug solution 30 past the seal(s) formed by the expandable member(s) 11, 12 at the end(s) of the treatment chamber. Alternatively, the pressure of the liquid drug solution 30 in the treatment chamber may be maintained at close to atmospheric pressure by the pump 67, or by a gravity-feed directly from the reservoir 66 without the use of a pump. Furthermore, instead of using the powered pump 67, the liquid drug solution 30 may be circulated through the closed fluid circuit by pushing a fixed volume of the liquid drug solution 30 between first and second external reservoirs, e.g., first and second syringes connected to the fluid connectors 15, 16, as mentioned above.

Figure 7:
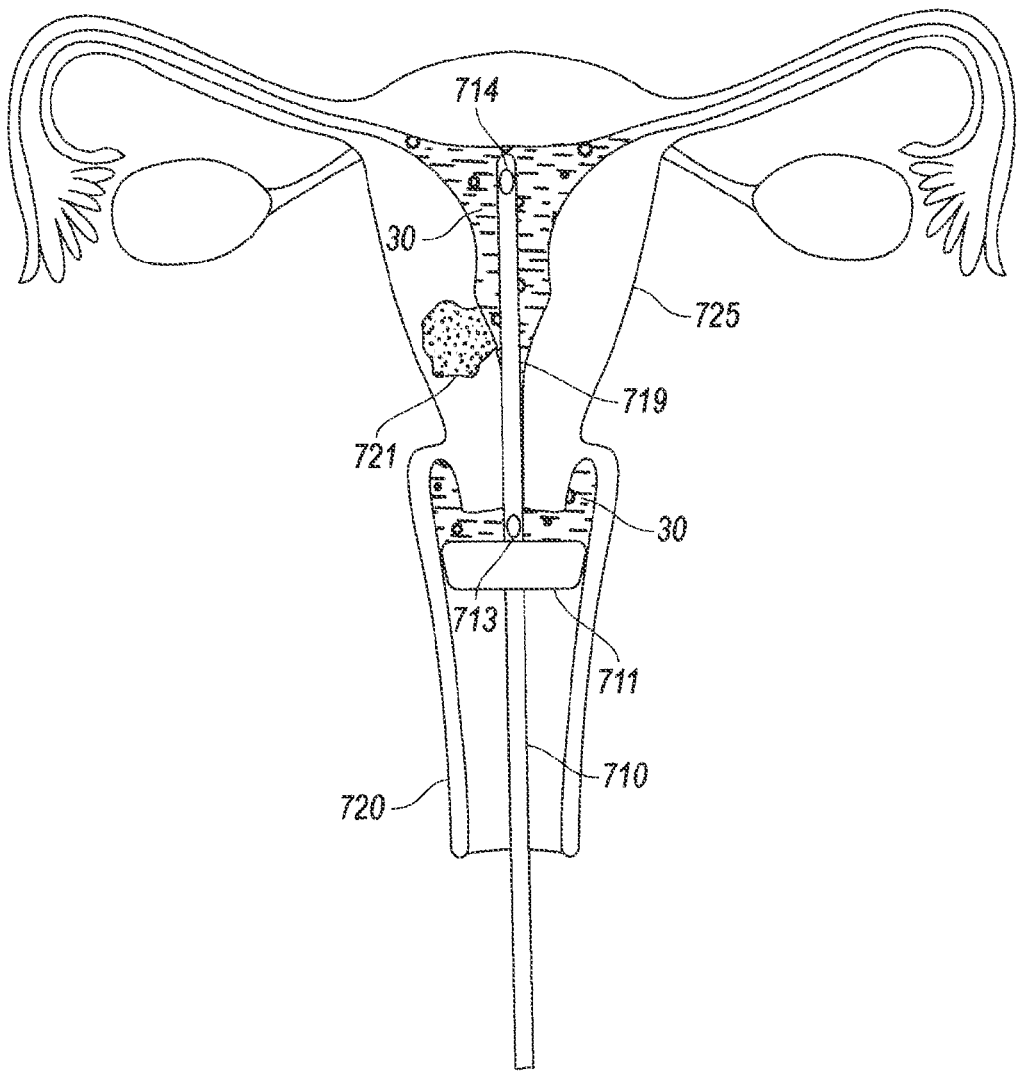
FIG. 7 illustrates a chemotherapeutic treatment of a portion of a female genital tract using a catheter in accordance with another embodiment of the disclosure.

FIG. 7 illustrates a catheter 710 in accordance with embodiments hereof. Catheter 710 is shown in a deployed configuration within a target region of a female genital tract including a portion of a vagina 720 and uterus 725. An expandable member 711 is mounted about a distal region 719 of the catheter 710 and is adapted to be expanded into sealing contact with the inner wall of the uterus 725, or, as illustrated, with the inner wall of the vagina 720. A treatment chamber is defined as the portion of the natural lumen or genital tract distal of the expandable member 711. In the illustrated embodiment, the treatment chamber includes a uterine cancer tumor 721. The catheter distal region 719 extends distally of the expandable member 711 by a length that may be fixed and selectively pre-designed or that may be variable and selectively adjusted by the operator, similar to length L in the catheter 10' described above and shown in FIG. 5. Port 713 is disposed distally adjacent of the expandable member 711 and port 714 is disposed at or adjacent the distal end of the distal region 719. In the illustrated embodiment, the expandable member 711 extends to the fundus of the uterus and thereby positions the port 714 at or near the distalmost extent of the desired treatment chamber. The ports 713, 714 fluidly communicate the treatment chamber with respective lumens (not shown) that extend proximally through the catheter to terminate at respective connectors located at the proximal end thereof, comparable to the fluid connectors 15, 16 shown in FIG. 6. This embodiment demonstrates a treatment chamber that is defined by the force of gravity and the location of the egress port 714. The proximal end of the treatment chamber may or may not be defined by an expandable member, as described below.

Once the catheter 710 has been deployed as shown in FIG. 7, the operator may assess the orientation of the treatment chamber with respect to gravity G, and may reposition the patient, if necessary, to orient the treatment chamber as close to vertical as possible, as described above with respect to the catheter 10 in FIG. 1. In the treatment illustrated in FIG. 7, the port 714 may be defined as the egress port and the port 713 may be defined as the ingress port. After the treatment chamber is oriented with respect to gravity, a liquid drug solution 30 is admitted or forced into the chamber via the ingress port, i.e. the port 713 in FIG. 7. As the liquid drug solution 30 fills the treatment chamber from bottom to top, air is purged from the chamber via the egress port, i.e. the port 714 until the liquid drug solution reaches the port 714. In this way, the treatment chamber is filled with the liquid drug solution 30, leaving only a small air bubble or preferably no bubble at all. The avoidance of air bubbles or air pockets may ensure that all of the inner wall of female genital tract in the treatment chamber is bathed in the liquid drug solution 30. The liquid drug solution 30 may be circulated or recirculated through the treatment chamber between the ingress port 713 and the egress port 714 as described above with respect to the embodiment shown in FIG. 1. Alternatively, the treatment chamber may be filled with the liquid drug solution 30 of a known, e.g. calculated drug concentration for a selected period of time without circulation or recirculation. The treatment chamber may also be evacuated, as described above, by forcing a flushing fluid therethrough using the ports 713, 714.

The extent of the treatment chamber formed in the hollow anatomical space may be controlled by limiting the volume or pressure of the liquid drug solution 30 admitted or forced into the treatment chamber via the catheter 710. In the example illustrated in FIG. 7, the liquid drug solution 30 has not been forced into the fallopian tubes from the uterus, although extending the treatment chamber into these spaces may be desirable for treatment of cancer in the fallopian tubes or the ovaries. Since the ostia of the fallopian tubes are proximate to but not in direct connection with the respective ovaries, any liquid drug solution 30 that is forced all the way through one or both fallopian tubes may enter and begin to fill the peritoneal cavity and may result in either intentional or unintentional intraperitoneal chemotherapy. The catheter 710 may be selectively designed or placed such that the expandable member 711 creates the proximal end of a treatment chamber in the uterus, or in the vagina, as illustrated. Thus, cancer in various locations throughout the female genital tract may be treated by exposing target tissue to the liquid drug solution 30. Alternatively, the catheters 10, 10' may be adapted to create a treatment chamber bounded at its ends by two or more expandable members selectively spaced apart and positioned along the female genital tract from the vaginal vestibule, through the cervix, to the fundus of the uterus. In another alternative in accordance with an embodiment of the present technology (not shown), a catheter or catheters may be adapted to operate solely or in combination to create a female genital tract treatment chamber wherein at least distal portions of one or both fallopian tubes are excluded therefrom by expandable member(s) deployed within the respective fallopian tube(s).

The catheter 710 features a single expandable member and two spaced-apart ports disposed distally thereof such that a treatment chamber for use in chemotherapy can be created distally of the expandable member. Further embodiments include catheters, systems, and methods wherein two ports are disposed proximally of a single expandable member such that a treatment chamber for use in chemotherapy can be created proximally of the expandable member.

Further embodiments include catheters, systems, and methods wherein a catheter having two spaced-apart ports but without any expandable member can seal within the cervix and thereby form a treatment chamber distally thereof, including the uterus. Such a balloonless catheter may be a modification of any catheter disclosed herein, for example the catheter 10' of FIG. 5 wherein the shaft 50 may be modified to fit sealably within the cervix, especially the cervix of a nulliparous female patient having a very small cervical opening.

Figure 8:
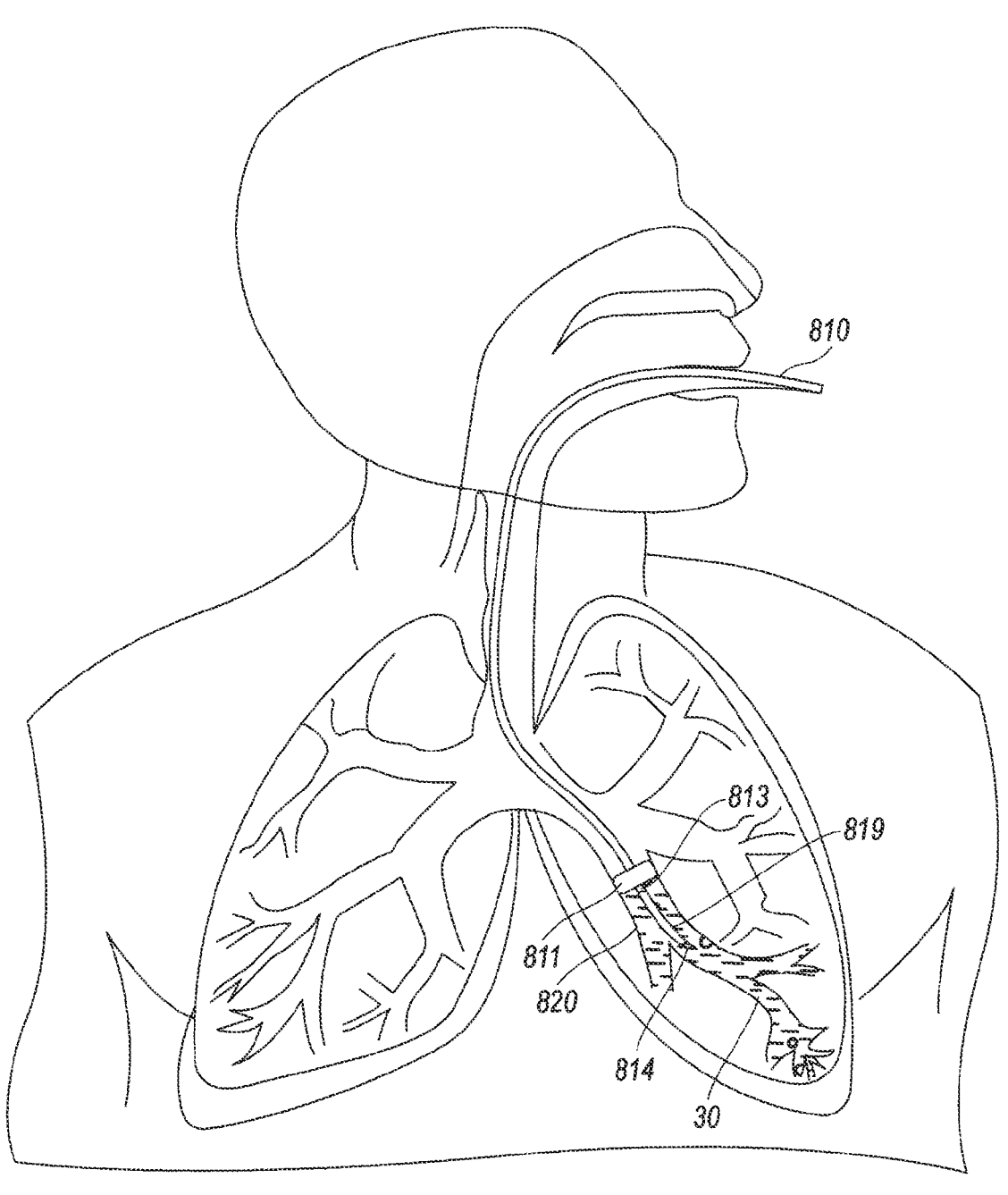
FIGS. 8-10 illustrate a chemotherapeutic treatment of a portion of a respiratory tract using a catheter in accordance with another embodiment of the disclosure.

FIG. 8 illustrates a catheter 810 configured in accordance with another embodiment of the present technology. The catheter 810 is shown in a deployed configuration within a target region of a respiratory tract. A catheter distal region 819 extends distally of an expandable member 811 by a length that may be fixed and selectively pre-designed or that may be variable and selectively adjusted by the operator, similar to length L in the catheter 10' described above and shown in FIG. 5. The expandable member 811 is mounted about the distal region 819 of catheter 810 and is adapted to be expanded into sealing contact with the inner wall of a segmental bronchus 820, as shown. A port 813 is disposed distal of and adjacent to the expandable member 811 and a port 814 is disposed at or adjacent the catheter distal end of distal region 819. A treatment chamber is defined as the portion of the natural lumen or respiratory tract distal of the expandable member 811. The catheter 810 may be adapted, if necessary, for creating treatment chambers in different parts of the bronchi of the respiratory tract. The structure and use of the catheter 810 is comparable to that of the catheter 710 described above and shown in FIG. 7. The patient may be repositioned as described above to optimize orientation of the treatment chamber for purging air therefrom, and the ports 813, 814 may be used in similar fashion to the ports 13, 14, 713, 714 as described above to purge air and to circulate or recirculate a liquid drug solution 30. The treatment chamber may also have air evacuated therefrom before treatment, and/or liquid drug solution cleared out by forcing a flushing fluid therethrough using the ports 813, 814.

Figure 9:
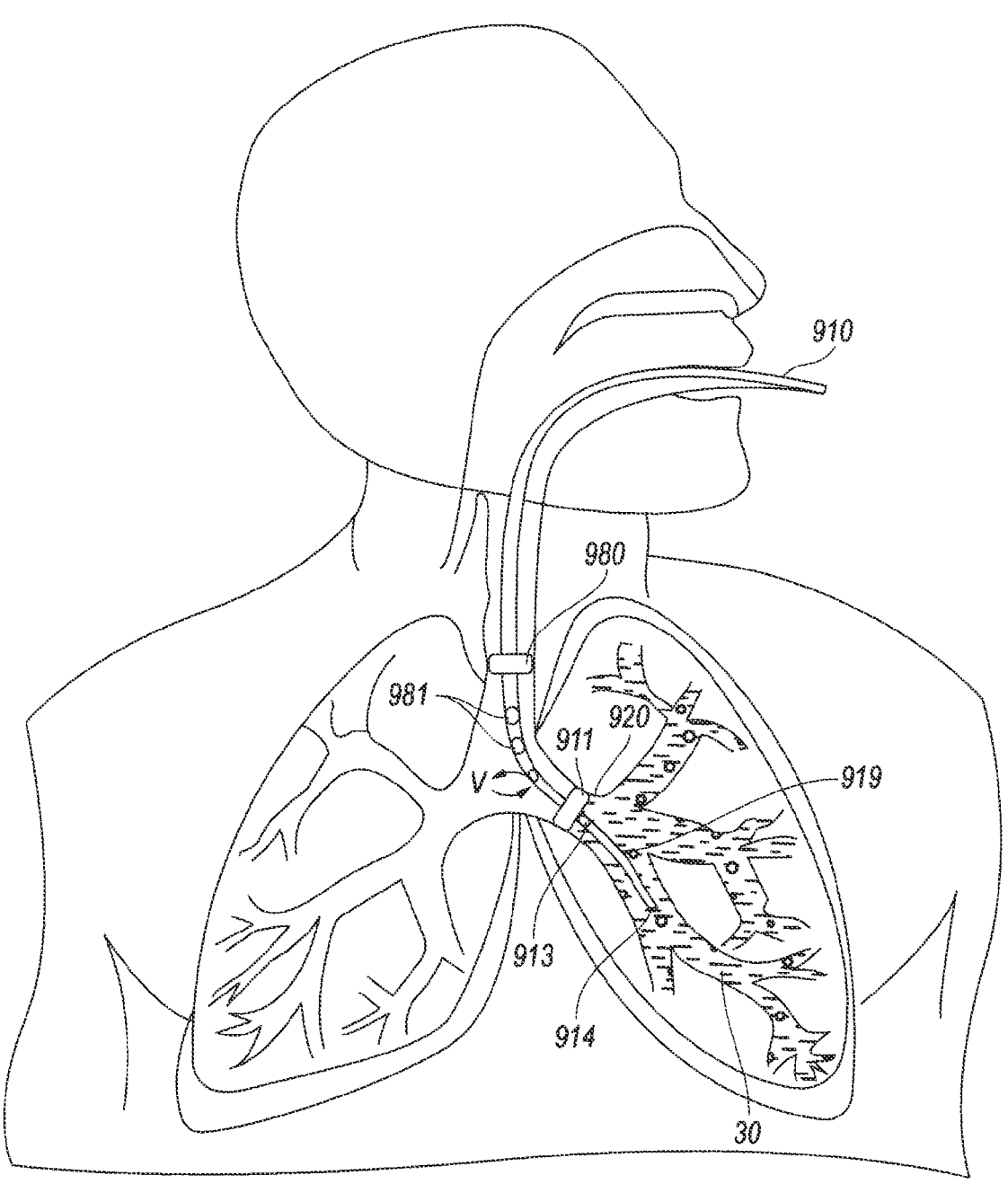

FIG. 9 illustrates a catheter 910 configured in accordance with another embodiment of the present technology. The catheter 910 is shown in a deployed configuration within a target region of a respiratory tract. A catheter distal region 919 extends distally of an expandable member 911 by a length that may be fixed and selectively pre-designed or that may be variable and selectively adjusted by the operator, similar to length L in the catheter 10' described above and shown in FIG. 5. The expandable member 911 is mounted about the distal region 919 of the catheter 910 and is adapted to be expanded into sealing contact with the inner wall of a main bronchus, e.g. a left main bronchus 920 as shown. A port 913 is disposed distal of and adjacent to the expandable member 911 and a port 914 is disposed at or adjacent the distal end of the catheter distal region 919. A treatment chamber is defined as the portion of the natural lumen or respiratory tract distal of expandable member 911. Catheter 910 may be adapted, if necessary, for creating treatment chambers in different parts, e.g. one or more branches of a bronchus of the respiratory tract.

The structure and use of the catheter 910 are comparable to those of the catheter 810 described above with the addition of an inflatable cuff 980 disposed proximally of the expandable member 911 such that the cuff 980 can be located above the carina of the trachea. The catheter 910 also has one or more ventilation ports 981 located between the cuff 980 and the expandable member 911. The ports 981 may fluidly communicate with a conventional medical ventilator machine via one or more dedicated lumens (not shown) through the catheter 910. While the treatment chamber is bathed in a liquid drug solution 30, the cuff 980 may be inflated to seal against the trachea and permit ventilation V of the non-treated lung, e.g. the right lung as shown in FIG. 9, via the ports 981. The patient may be repositioned as described above to optimize orientation of the treatment chamber for purging air therefrom, and the ports 913, 914 may be used in similar fashion to ports the 13, 14, 813, 814 as described above to purge air and to circulate or recirculate the liquid drug solution 30. The treatment chamber may also have air evacuated therefrom before treatment, and/or the liquid drug solution 30 cleared out by forcing a flushing fluid therethrough using the ports 913, 914. The catheter 910 may be repositioned to permit sequential treatment of left and right respiratory tracts or super-selective treatment of individual bronchi or bronchioles as described below. Alternatively, a similar treatment may be performed by using the catheter 810 as described above and simultaneously placing a conventional endotracheal tube such that the inflatable cuff thereof seals around the shaft of the catheter 810 and against the trachea to permit ventilation of the non-treated lung.

A highly localized method of chemotherapy may reduce sequelae and increase effectiveness for drug treatments. As described herein, a computer system, such as that shown in FIG. 18, may be used to optimize treatment of a tumor area while minimizing exposure of otherwise healthy tissue to powerful treatment drugs. Continuing with the lung cancer example of the disclosure, FIGS. 13-17 show simplified tracheobronchial airway diagrams labeled with Strahler stream order numbers reflecting branching complexity. Although human pulmonary anatomy may typically have approximately 23 Strahler orders, only three Strahler orders are shown in FIGS. 13-17 for ease of illustration. Besides the Strahler system, mathematical models of the morphology of the human bronchial tree have also been developed by others such as Weibel; Horsfield and Cumming; Horsfield, Dart, Olson, Filley and Cumming; etc. Such mathematical models may be used by computer software in calculating anatomical and/or physiological variables that are useful for planning and conducting super selective drug treatment in the hierarchical respiratory system.

Figure 13:
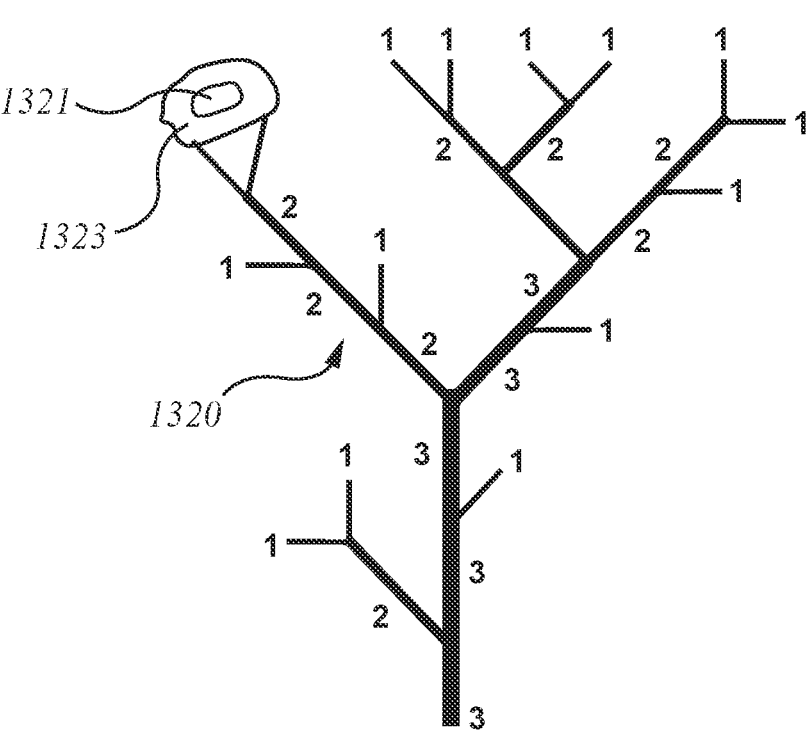
FIGS. 13-17 are diagrams showing a simplified tracheobronchial airway labeled with Strahler stream order numbers reflecting branching complexity. A cancer tumor is shown relative to the airway.
Figure 14:
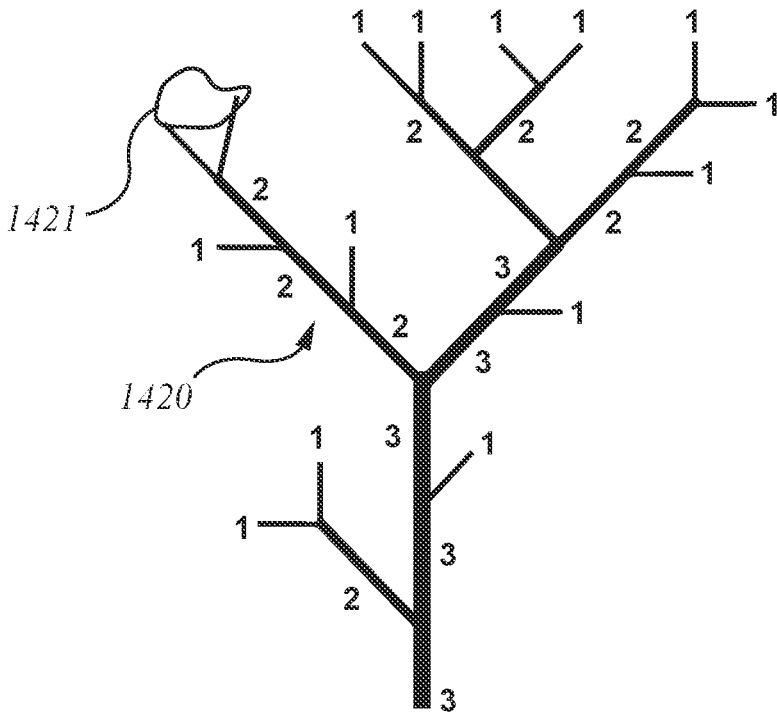

In FIG. 13, a cancer tumor 1321 is shown relative to an airway 1320. Because the cancer tumor 1321 is spaced apart from the nearest segment(s) of the airway 1320, a larger zone 1323 of lung tissue surrounding tumor 1321 may be included in the treatment plan such that a liquid drug 30 permeates the zone 1323 to reach and penetrate the cancer tumor 1321. In FIG. 14, because the cancer tumor 1421 is disposed adjacent to segments of an airway 1420, the cancer tumor 1421 may be treatable directly with reduced effect on surrounding healthy tissue and possibly with a smaller-sized treatment zone than would be required in treatment of the cancer tumor 1321 in FIG. 13. Tumor treatment zone size can be matched exactly to the tumor or may include a region beyond the tumor. Alternatively, a treatment zone may be restricted to be less than the tumor. A treatment zone that is greater or less than the actual tumor size can be based on the distance (cm) from an airway to the tumor, or the zone size may be calculated as a percentage of the tumor size. Other methods may be used to calculate the size of the intended treatment zone.

Figure 15:
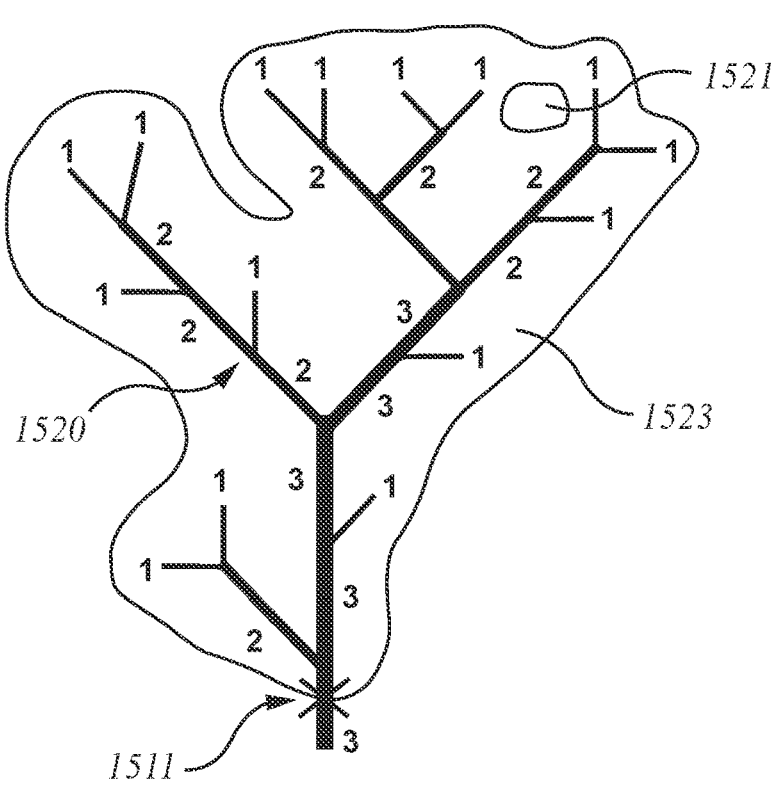

FIG. 15 illustrates applying drug treatment to a respiratory tract of a lung, as may be performed according to the disclosure without using computer software to plan and optimize the treatment. A cancer tumor 1521 is shown disposed between two airways each having a Strahler number one (1). A catheter in accordance with the disclosure (not shown) may be positioned such that an expandable member is located at a proximal airway treatment position 1511 having a Strahler number three (3). A treatment zone 1523 for permeation by a drug is defined as the lung tissue surrounding the entire portion of a respiratory airway 1520 distal of the treatment position 1511. Such a treatment could unnecessarily subject non-diseased lung tissue to penetration by a chemotherapeutic drug.

Figure 16:
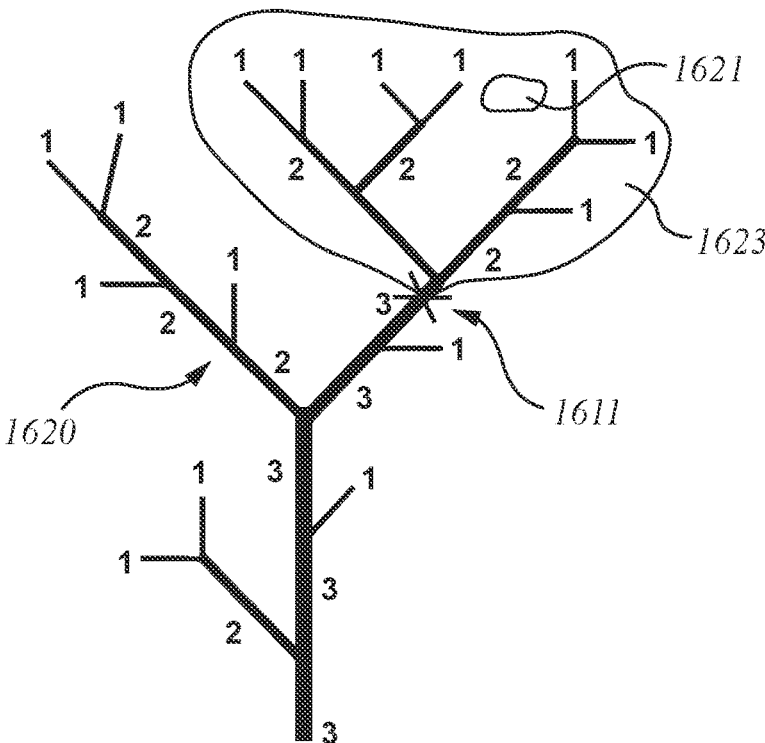

FIG. 16 illustrates applying drug treatment to a respiratory tract of a lung using computer software in accordance with the disclosure and as described below. A cancer tumor 1621 is located similarly to tumor 1521 in FIG. 15 between two airways each having a Strahler number one (1). A catheter in accordance with the disclosure (not shown) may be positioned such that an expandable member is located at a single distal airway treatment position 1611 having a Strahler number three (3). A treatment zone 1623 for permeation by a drug is defined as the lung tissue surrounding the portion of a respiratory airway 1620 distal of the treatment position 1611. Such a selective treatment guided by computer software could avoid subjecting extensive non-diseased lung tissue to penetration by a chemotherapeutic drug.

Figure 17:
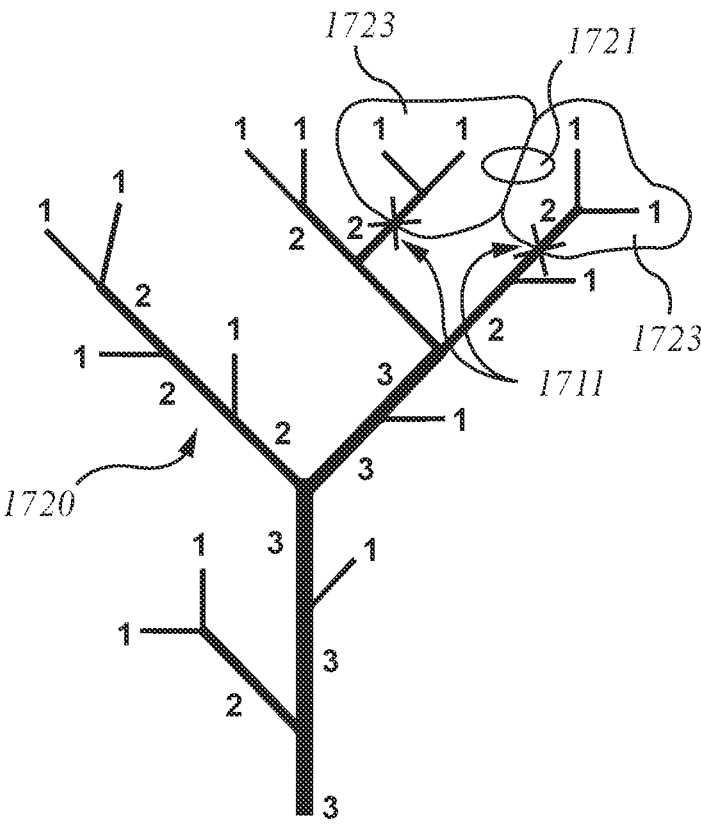

FIG. 17 illustrates applying drug treatment to a respiratory tract of a lung using computer software in further accordance with the disclosure and as described below. A cancer tumor 1721 is located similarly to the cancer tumors 1521 and 1621 between two airways each having a Strahler number one (1). A catheter in accordance with the disclosure (not shown) may be sequentially positioned such that an expandable member is located at multiple distal airway treatment positions 1711 having a Strahler number two (2). Two treatment zones 1723 for permeation by a drug are defined as the lung tissue surrounding the two portions of airway 1720 distal of the treatment positions 1711. The treatment zones 1723 are shown as abutting each other and encompassing all of the cancer tumor 1721. Alternatively, the treatment zones 1723 can overlap to ensure that all of the cancer tumor 1721 is saturated with drug. If less than 100% saturation of the cancer tumor 1721 is clinically desired, then the treatment zones 1723 can be limited in size and shape, e.g. by changing the treatment positions 1711 in a respiratory airway 1720 and/or limiting the dwell time of drug in the airway. The computer software may determine that more than two treatment zones may be effective depending on the anatomy of the airway. Treatment location selection may be limited by the diameter of the treatment device such that only airways of a minimum diameter may be considered. Such a super selective treatment, guided by computer software, may avoid subjecting non-diseased lung tissue to penetration by a chemotherapeutic drug. The catheter 910 may be modified for simultaneous bilateral treatment of the lungs. Instead of the ports 981 being in communication with a ventilator for ventilating the non-treated lung, ports disposed between the cuff 980 and the expandable member 911 may be located and connected to perform ingress and egress functions similar to the ports 13, 14, 713, 714 as described above to purge air and to circulate or recirculate the liquid drug solution 30. Thus, while one treatment chamber receives drug treatment, e.g., a portion of the left lung distal of the expandable member 911, the entire respiratory tract of the contralateral lung, e.g., right lung can become a second treatment chamber in fluid communication with the space between the cuff 980 and the expandable member 911.

Figure 18:
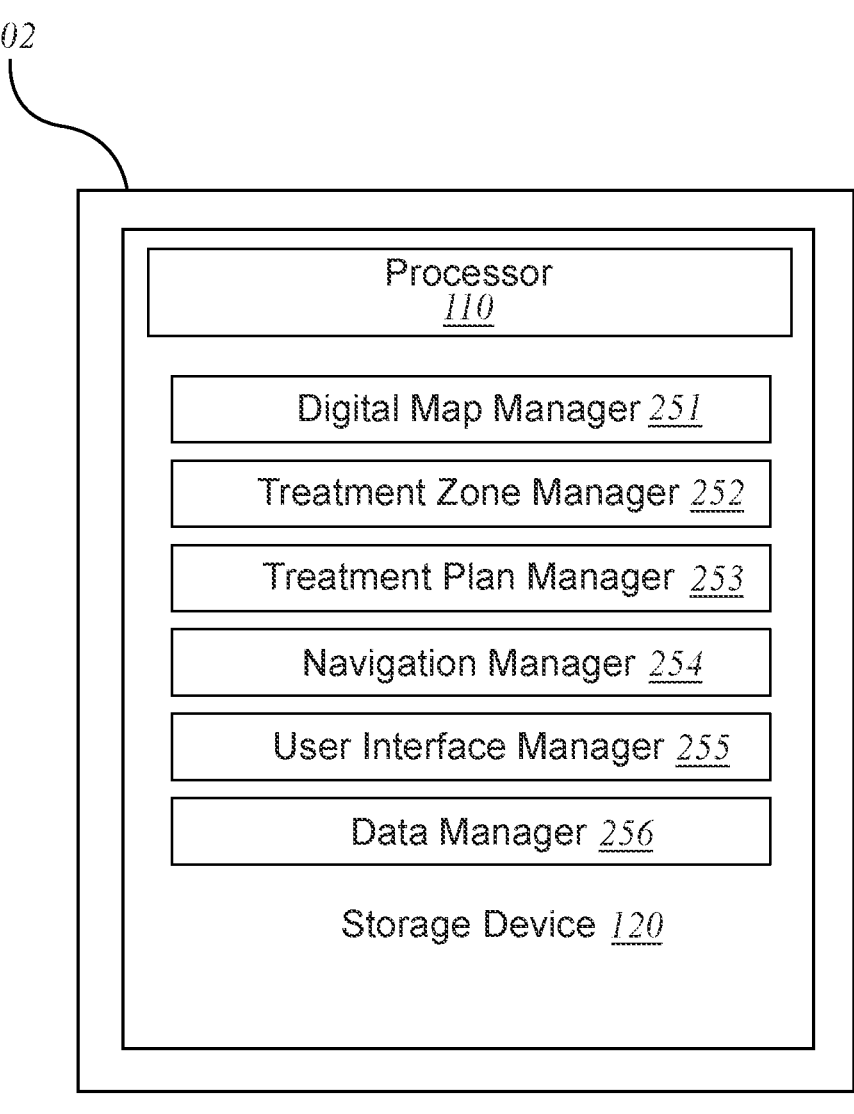
FIG. 18 illustrates a tumor treatment computer system consistent with embodiments hereof.

FIG. 18 illustrates a tumor treatment computer system configured for procedural planning and navigation according to embodiments hereof. The tumor treatment computer system includes hardware and software configured for tumor treatment planning. To identify airways and cancer tumors, an initial digital map may be created in a computer by non-invasive imaging techniques such as computerized tomography (CT), magnetic resonance (MR), positron emission tomography (PET), etc. The software can analyze the digital map and evaluate the proximity of one or more airways to a tumor. The software can look for direct overlap or proximity of airways to a tumor to define a tumor treatment zone, which can be done in a two-dimensional (2D) or three-dimensional (3D) manner. Those airways that meet the proximity requirements can be backtracked towards the trachea to identify one or more potential treatment locations that the clinician can select. Software can automatically determine locations by solving for number of treatment locations (1, 2, etc.). Software can be used for procedural planning before a treatment procedure and/or for navigation during the procedure.

The tumor treatment computer system 102 may be configured for tumor treatment planning and for navigation during a tumor treatment procedure. The tumor treatment computer system 102 may be configured as a server (e.g., having one or more server blades, processors, etc.), a personal computer (e.g., a desktop computer, a laptop computer, etc.), a smartphone, a tablet computing device, computing hardware integral to a surgical system, and/or other device. In an embodiment, any, or all of the functionality of the tumor treatment computer system 102 may be performed as part of a cloud computing platform.

The tumor treatment computer system 102 includes one or more processors 110 (also interchangeably referred to herein as processors 110, processor(s) 110, or processor 110 for convenience), one or more storage device(s) 120, and/or other components. In other embodiments, the functionality of the processor may be performed by hardware (e.g., through the use of an application specific integrated circuit ("ASIC"), a programmable gate array ("PGA"), a field programmable gate array ("FPGA"), etc.), or any combination of hardware and software.

A storage device 120 may include any type of non-transitory computer readable storage medium (or media) and/or non-transitory computer readable storage device. Such non-transitory computer readable storage media or devices may store computer readable program instructions for causing a processor to carry out one or more methodologies described here. Examples of the computer readable storage medium or device may include, but are not limited to an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples.

The processor 110 may be programmed by one or more computer program instructions stored on a storage device 120. For example, the processor 110 is programmed by a digital map manager 251, a treatment zone manager 252, a treatment plan manager 253, a navigation manager 254, a user interface manager 255, and a data manager 256. It will be understood that the functionality of the various managers as discussed herein is representative and not limiting. As used herein, for convenience, the various "managers" will be described as performing operations, when, in fact, the managers program the processor 110 (and therefore the tumor treatment computer system 102) to perform the operations. When implemented as software instructions, the functionality of the various managers discussed herein may be divided differently between the described managers and/or between different managers. The various components of the tumor treatment computer system 102 work in concert to provide tumor treatment planning and procedural navigation, as discussed below.

In embodiments, various aspects of the tumor treatment computer system 102 may be instantiated or operated on different computing systems. For example, in an embodiment, a first tumor treatment computer system 102 may operate to develop a tumor treatment plan via the actions of the digital map manager 251, the treatment zone manager 252, the treatment plan manager 253, the user interface manager 255 and the data manager 256. The treatment plan may be stored and accessed via a second tumor treatment computer system 102. The second tumor treatment computer system 102 may be operated to conduct a tumor treatment procedure according to the treatment plan using the navigation manager 254, the user interface manager 255, and the data manager 256. Thus, the operational aspects of the tumor treatment computer system 102, as described herein, may be carried out by multiple computer devices.

The digital map manager 251 is a software protocol operating on the tumor treatment computer system 102. The digital map manager is configured to create a digital map identifying one or more lung cancer tumors and one or more respiratory airways proximate to the one or more lung cancer tumors. The digital map manager is configured to interact with the data manager 256 to access image data suitable for creating the digital map. The digital map includes at least the lung cancer tumors and the respiratory airways, including their sizes, shapes, and locations in two and/or three-dimensional space. The digital map may further include more anatomical details as well. The digital map is a 2D or 3D rendering of at least the respiratory airways and the lung cancer tumors.

The treatment zone manager 252 is a software protocol operating on the tumor treatment computer system 102. The treatment zone manager 252 is configured to analyze the digital map created by the digital map manager 251. The analysis of the digital map may be performed in a two-dimensional (2D) or three-dimensional (3D) manner. According to the analysis, the treatment zone manager 252 is further configured to define one or more tumor treatment zones and/or one or more treatment positions for permeation of a drug into lung tissue surrounding portions of the one or more respiratory airways. The treatment zone manager 252 is configured to define a treatment zone sufficient to treat a lung cancer tumor and to define the corresponding treatment position. Treatment zones and/or treatment positions may be defined successively or simultaneously. Because the treatment zones depend on the treatment position, a given treatment zone corresponds to a specific treatment position. For example, the treatment zone manager 252 may define a treatment zone sufficient to treat a lung cancer tumor and then determine the corresponding treatment position necessary to create the treatment zone. In another example, a treatment position may be selected by the treatment zone manager 252 and, based on the treatment position, a treatment zone may be defined.

As discussed above with respect to FIGS. 13 and 14, the treatment zone manager 252 may be configured to define one or more tumor treatment zones and one or more treatment positions to minimize or reduce the amount of extraneous tissue affected by chemotherapeutic drug solutions based on the respiratory airway pathways identified in the digital map produced by the digital map manager 251.

Each treatment position is defined by the treatment zone manager 252 as a location at which chemotherapeutic drug solutions are to be delivered. The treatment positions are selected so as to generate the one or more tumor treatment zones when the chemotherapeutic drug solution or drug is delivered at the treatment position. The tumor treatment zones are located distally within the respiratory airway system of the treatment positions. For example, as shown in FIG. 16, drug delivered at treatment position 1611 results in tumor treatment zone 1623, which surrounds cancer tumor 1621. In another example, as shown in FIG. 17, drug delivered at treatment positions 1711 results in two tumor treatment zones 1723 that abut or overlap one another and, together, provide drug treatment to an entirety of cancer tumor 1721.

In embodiments, tumor treatment zones and treatment positions may be defined as follows. The treatment zone manager 252 may be configured to identify direct overlap of one or more respiratory airways to a tumor and/or to identify proximity of one or more respiratory airways to a tumor. Proximity may be determined according to a predefined proximity threshold value. By identifying locations of overlap and/or proximity of one or more respiratory airways to a tumor, the treatment zone manager 252 may determine a treatment position and a tumor treatment zone. Based on the identified respiratory airways that overlap or are proximate to a tumor, the treatment zone manager 252 selects a treatment position proximal to the location of overlap or proximity within the identified respiratory airways. Drug delivered at such a proximal position will fill the chamber created distal of the treatment position in the respiratory airways and permeate into the surrounding tissue to generate a tumor treatment zone appropriate for treating that tumor. Such a proximal treatment position is selected by backtracking through the airways from the location of overlap or proximity to the tumor. Backtracking may be performed to determine a treatment position and/or a treatment zone. Backtracking may be performed until the tumor treatment zone provided by the identified treatment position is large enough to cover an entirety of the tumor. Thus, the treatment zone manager 252 may be configured to successively analyze positions that are progressively more proximal within the respiratory airway from the overlap/proximity location until a suitable treatment position is identified.

In embodiments, multiple treatment positions may be identified by backtracking from multiple overlap/proximity locations and an operator or clinician may select which treatment positions to use in generating a treatment plan. For example, if one airway wraps around the front of a tumor and another airway wraps around the back of a tumor, the treatment zone manager 252 may determine a combination of treatment positions based on overlap/proximity locations in each airway.

In embodiments, defining the one or more tumor treatment zones may be performed by identifying or determining two tumor treatment zones surrounding portions of two different respiratory airways. The two tumor treatment zones may abut or overlap each other to provide drug treatment of at least one tumor, as discussed with respect to FIG. 17. In such embodiments, the treatment zone manager 252 may concurrently backtrack from two different overlap/proximity locations in different respiratory airways until the combination of the two different tumor treatment zones is sufficient to provide the necessary therapy.

In embodiments, each of the one or more tumor treatment zones is defined to provide drug treatment of an entirety of a respective one of the one or more lung cancer tumors while minimizing drug treatment of non-cancerous tissue. In further embodiments, the one or more treatment zones may be defined to provide drug treatment to a volume extending beyond the edges of the tumor. In alternative embodiments, each of the one or more tumor treatment zones is defined to provide drug treatment of less than an entirety of a respective one of the one or more lung cancer tumors while minimizing drug treatment of non-cancerous tissue. Less than an entirety may be treated, for example, to avoid treating excess amounts of healthy tissue.

In embodiments, a clinician or other operator may interact with the tumor treatment computer system 102, e.g., via the user interface manager 255, during development of the tumor treatment zones. In an embodiment, a clinician may select between multiple defined tumor treatment zones, as discussed above. In a further embodiment, a clinician may adjust a defined tumor treatment zone or tumor treatment position and review the projected results. For example, where a defined tumor treatment zone encompasses a portion of tissue that a clinician does not want to treat, the clinician may manually adjust the treatment position until the defined tumor treatment zone better matches the intention of the clinician. Such manual intervention may be used to enlarge tumor treatment zones, shrink tumor treatment zones, or otherwise alter the size and shape of the tumor treatment zones.

In embodiments, the treatment zone manager 252 is configured to use clinician inputs when determining a treatment plan. Such inputs may include one or more of, a drug delivery distance from a tumor edge, a maximum number of defined treatment positions in a single treatment plan, a treatment margin exceeding a tumor margin, and a minimum diameter of a respiratory airway for placement of a drug delivery catheter. Each of these clinician selectable inputs may be used in determining the tumor treatment zones and treatment positions. In embodiments, default values for each of these inputs may be used if a clinician or operator does not make a selection.

The treatment plan manager 253 is a software protocol operating on the tumor treatment computer system 102. The treatment plan manager 253 is configured to generate a treatment plan according to the one or more treatment zones defined by the treatment zone manager 253.

In embodiments, the treatment plan manager 253 is configured to define one or more proposed routes for navigation of a drug-delivery catheter through a respiratory airway system to the defined treatment position in each of the one or more respiratory airways and to include the one or more proposed routes in the treatment plan. In embodiments where multiple treatment positions are proposed or defined, multiple navigation routes may be defined.

In embodiments, the treatment plan manager 253 is further configured to provide one or more potential treatment plans for selection by a clinician. One or more viable potential treatment plans may be developed by the treatment plan manager 253 to permit a clinician the opportunity to select which plan to execute. Multiple treatment plans may be beneficial to take advantage of a clinician or operator's experience and knowledge. As discussed above, the treatment zone manager 252 may identify multiple potential treatment positions and corresponding tumor treatment zones. Each of these may be presented to a clinician or operator during treatment plan determination.

The navigation manager 254 is a software protocol operating on the tumor treatment computer system 102. The navigation manager 254 is configured to access the tumor treatment plan and/or any proposed navigation routes generated by the treatment plan manager 253. The navigation manager 254 is further configured to interface with catheter systems so as to guide manual or robotic placement of a drug delivery catheter to the defined treatment position in each of the one or more respiratory airways. Manual placement may be guided by providing a clinician with a respiratory map illustrating treatment positions and/or navigation routes that a clinician may follow while navigating a drug delivery catheter. Robotic placement may be guided by providing robotic control instructions to a robotic catheter system.

The user interface manager 255 is a software protocol operating on the tumor treatment computer system 102. The user interface manager 255 is configured to provide a user interface to allow user interaction with the tumor treatment computer system 102. The user interface manager 255 is configured to receive input from any user input source, including but not limited to touchscreens, keyboards, mice, controllers, joysticks, voice control. The user interface manager 255 is configured to provide a user interface, such as a text based user interface, a graphical user interface, or any other suitable user interface.

The data manager 256 is a software protocol operating on the tumor treatment computer system 102. The data manager 256 is configured to access, receive, or obtain image data, including image data. The image data may include data acquired via non-invasive imaging of a lower respiratory tract or other relevant physiological location and may include computerized tomography (CT) image data, magnetic resonance (MR) image data, positron emission tomography (PET) image data, and any other type or format of suitable image data used for identifying and locating tumors. The data manager 256 may be configured to interface with other computing devices and systems as required to access, receive, or obtain the image data. The data manager 256 is further configured to access the storage device 120 to store and/or receive image data stored on the storage device 120. The data manager 256 may provide data to a user via the user interface manager 255. In embodiments, the data manager 256 is further configured to provide access tools to the user to manage and manipulate image data.

Figure 19:
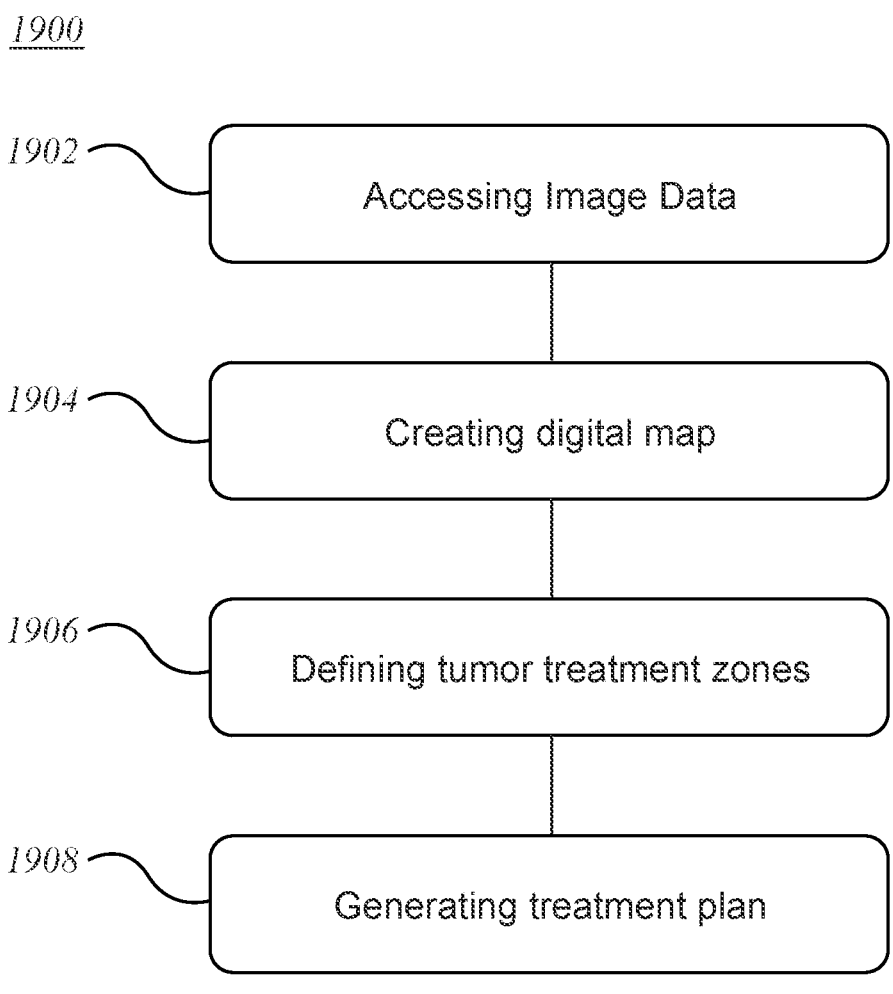
FIG. 19 illustrates a method of tumor treatment planning consistent with embodiments hereof.

FIG. 19 is a flow chart showing a process 1900 of preparing a tumor treatment plan. The process 1900 is performed on a computer system having one or more processing units programmed with computer program instructions that, when executed by the one or more processing units (i.e., processors), cause the computer system to perform the method. In embodiments, the process 1900 is carried out via the tumor treatment computer system 102 as described herein. The tumor treatment computer system 102 represents an example of a hardware and software combination configured to carry out process 1900, but implementations of the process 1900 are not limited to the hardware and software combination of the tumor treatment computer system 102. Additional details regarding each of the operations of the method may be understood according to the tumor treatment computer system 102, as described above.

In an operation 1902, the process 1900 includes accessing image data acquired by non-invasive imaging of a lower respiratory tract of a patient. The tumor treatment computer system 102 is used to access, obtain, receive, or otherwise acquire the image data obtained via non-invasive image. The image data may be obtained, for example, via one or more of a computerized tomography (CT) system, magnetic resonance imaging (MM) system, and a positron emission tomography (PET) system.

In an operation 1904, the process 1900 includes creating, according to the image data, a digital map identifying one or more lung cancer tumors and one or more respiratory airways proximate to the one or more lung cancer tumors. The digital map is a 2D or 3D digital rendering of at least the one or more respiratory airways and the one or more lung cancer tumors. The tumor treatment computer system 102 is used to create the digital map according to the accessed image data.

In an operation 1906, the process 1900 includes defining, according to an analysis of the digital map, one or more tumor treatment zones for permeation of a drug into lung tissue surrounding portions of the one or more respiratory airways. The tumor treatment zones are distal of treatment positions that are also defined during the operation 1906. The tumor treatment computer system 102 is used to define the one or more tumor treatment zones and the treatment positions. The treatment positions are located in the one or more respiratory airways such that, when treatment in the form of a chemotherapeutic drug solution is delivered at the treatment position, the chemotherapeutic drug solution fills the chamber formed in the respiratory airways and permeates into the surrounding tissue to treat the defined tumor treatment zones.

In embodiments, defining the tumor treatment zones and treatment positions may be influenced by various clinician selectable inputs, such as drug delivery distance from a tumor edge, a treatment margin exceeding a tumor margin, a maximum number of defined treatment positions in a single treatment plan, and a minimum diameter of a respiratory airway for placement of a drug delivery catheter. In embodiments, default values for each of these inputs may be used.

In an operation 1908, the process 1900 includes generating a treatment plan according to the one or more tumor treatment zones. The treatment plan is generated by the tumor treatment computer system and includes at least the tumor treatment zones and the treatment positions. In embodiments, the process 1900 may include generating multiple treatment plans for selection by a clinician.

Figure 10:
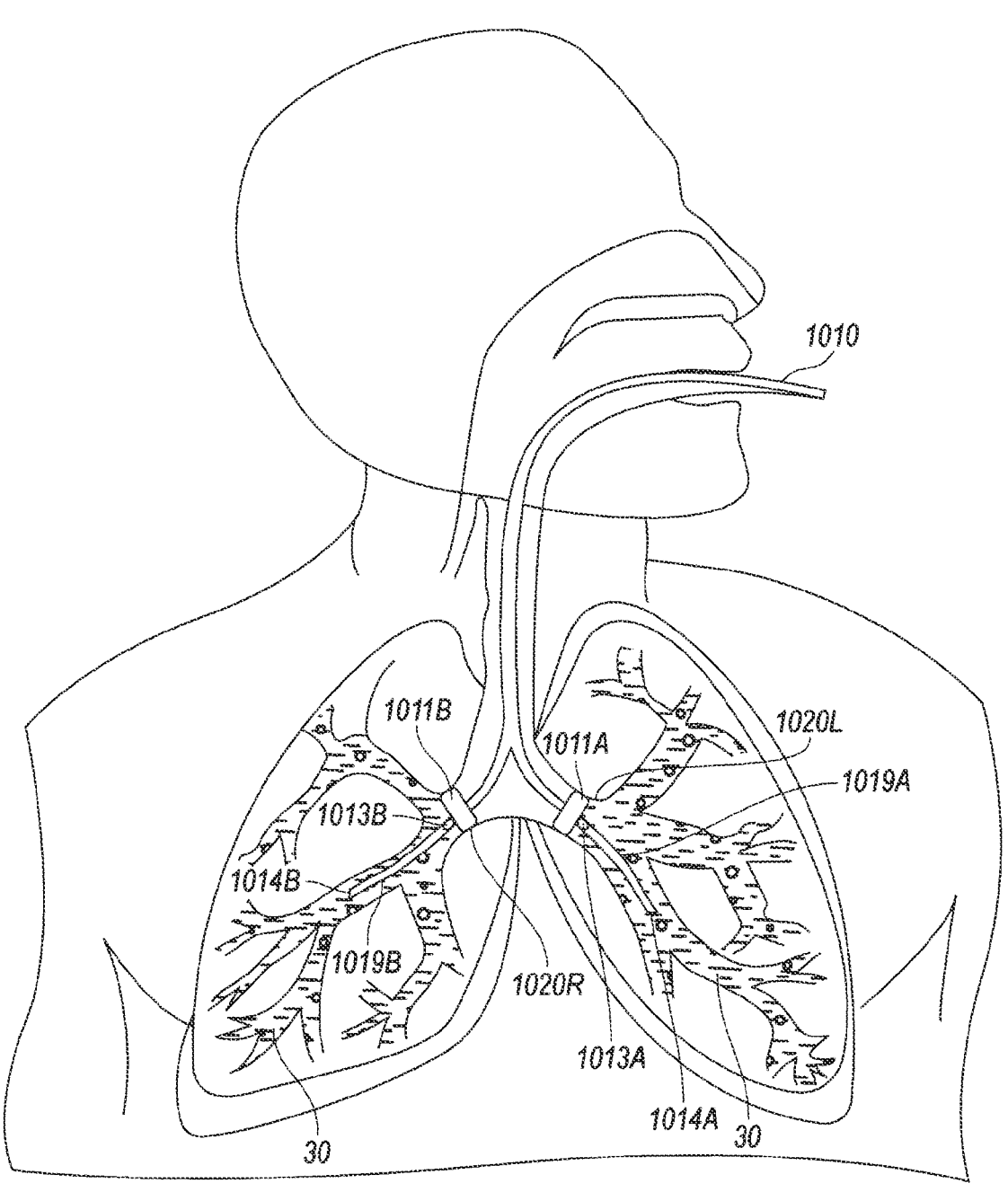

FIG. 10 illustrates a catheter 1010 configured in accordance with another embodiment of the present technology. The catheter 1010 is bifurcated and is shown in a deployed configuration suitable for simultaneous bilateral treatment of target regions, e.g., left and right, of a respiratory tract. Bilateral, or other dual treatments may be performed sequentially or overlapping in time without having to replace or reposition the catheter 1010, as for example in applying drug to treatment zones 1723 shown in FIG. 17. A catheter distal region 1019A of a first catheter branch extends distally of an expandable member 1011A by a length that may be fixed and selectively pre-designed or that may be variable and selectively adjusted by the operator, similar to length L in the catheter 10' described above and shown in FIG. 5. The expandable member 1011A is mounted about the distal region 1019A of the catheter 1010 and is adapted to be expanded into sealing contact with the inner wall of a segmental bronchus 1020L, as shown. A port 1013A is disposed distal of and adjacent to the expandable member 1011A and a port 1014A is disposed at or adjacent the distal end of the distal region 1019A. A treatment chamber is defined as the portion of the natural lumen or respiratory tract distal of the expandable member 1011A. Similarly, a catheter distal region 1019BA of a second catheter branch extends distally of an expandable member 1011B by a length that may be fixed and selectively pre-designed or that may be variable and selectively adjusted by the operator, similar to length L in the catheter 10' described above and shown in FIG. 5. The expandable member 1011B is mounted about the distal region 1019B of the catheter 1010 and is adapted to be expanded into sealing contact with the inner wall of a segmental bronchus 1020R, as shown. A port 1013B is disposed distal of and adjacent to the expandable member 1011B and a port 1014B is disposed at or adjacent the distal end of the distal region 1019B. A treatment chamber is defined as the portion of the natural lumen or respiratory tract distal of the expandable member 1011B. The catheter 1010 may be adapted, if necessary, for creating treatment chambers in different parts of the bronchi of the respiratory tract. The structure and use of the catheter 1010 are comparable to that of the catheter 810 described above and shown in FIG. 8 with the addition of a second distal catheter branch. The patient may be repositioned as described above to optimize orientation of the treatment chambers for purging air therefrom, and the ports 1013A, 1013B, 1014A, and 1014B may be used in similar fashion to ports the 13, 14, 813, 814 as described above to purge air and to circulate or recirculate liquid drug solution 30. The bilateral treatment chambers may also have air evacuated therefrom before treatment, and/or liquid drug solution cleared out by forcing a flushing fluid therethrough using the ports 1013A, 1013B, 1014A, and 1014B.

Figure 11:
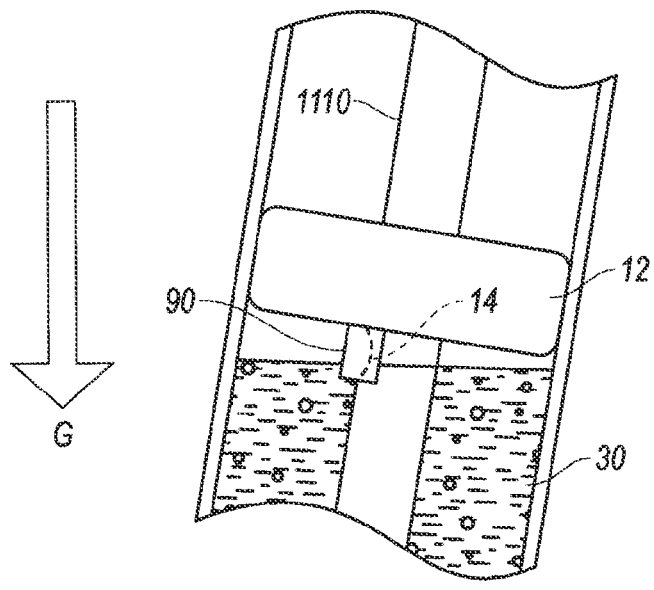
FIGS. 11 and 12 illustrate devices for membrane degasification of a liquid drug solution in accordance with another aspect of the disclosure.

FIG. 11 illustrates a portion of a catheter 1110 in accordance with an embodiment of the disclosure wherein an exemplary egress port 14 incorporates a membrane 90 to facilitate a procedure of filling a treatment chamber. The catheter 1110 is otherwise similar to the catheter 10, and if the functions of the port 13 (not shown) and port 14 are expected to be reversed, then the membrane 90 may be located at the port 13 instead of the port 14. The membrane 90 is permeable to gases but is impermeable to liquid. For example, the membrane 90 will allow air to pass, but not drug solutions for chemotherapy, hormonal therapy, or targeted drug/biologic therapy usable with the technology of the disclosure. As described above with regard to the embodiment of FIG. 1, the liquid drug solution 30 fills the treatment chamber from the bottom to the top with respect to gravity G, and air is purged from the chamber via the egress port, i.e. the port 14 until the liquid drug solution 30 reaches the membrane 90 at the port 14. See flow arrows F in FIG. 1. Filling the treatment chamber of the catheter 1110 via an ingress port 13 can automatically stop when the liquid drug solution 30 reaches the membrane 90 at the port 14. This self-limiting filling feature may be particularly useful for treatments where the drug solution will not be circulated or recirculated, but instead will remain stationary in the treatment chamber for a duration that is expected to achieve the desired drug dosing. Alternatively, the port on the catheter 1110 can serve as the primary air evacuation route as the chamber is filled and liquid may be replaced intermittently by evacuation and refilling via the ingress port 13. During evacuation of the liquid drug solution 30 from the treatment chamber via the ingress port 13, air or other gases may be admitted to the chamber via the egress port 14 and the membrane 90.

As illustrated in FIG. 6, the ports 13, 14 of the catheter 10 fluidly communicate the treatment chamber with respective lumens (not shown) that extend proximally through the catheter to terminate at the respective fluid connectors 15, 16 located at the proximal end thereof. However, the egress port of the catheter 1110 need not communicate all the way to the proximal end of catheter 1110. Air or gases purged through the membrane 90 and the egress port 14 may be exhausted from any point on the catheter shaft proximal to the treatment chamber. For example, the catheter 910 of FIG. 9 may be modified such that the egress port 913 may vent purged air through a membrane 90 as shown in FIG. 11 from the treatment chamber through a short catheter lumen that terminates in a modified port 98 located in the patient's trachea. Similarly, for treatment in any natural non-vascular body lumen, gases may be evacuated from the treatment chamber through a gas-permeable membrane and a port located at a chamber high point with respect to gravity, the gases passing through a dedicated vent lumen that terminates in an exhaust port on the catheter located anywhere outside of the treatment chamber.

Figure 12:
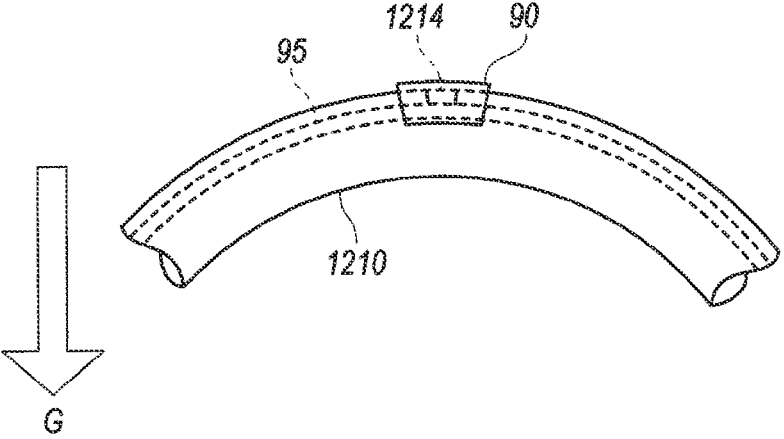

FIG. 12 illustrates a portion of a catheter 1210 in accordance with an embodiment of the disclosure wherein membrane 90 is associated with a vent port 1214. A lumen 95 is part of a fluid circuit carrying a liquid drug solution through the catheter 1210. As shown, the catheter 1210 is positioned such that the vent port 1214 is located at a high point in the catheter 1210 with respect to gravity G. This condition may occur or be caused to occur regardless of where the vent port 1214 is located on the catheter 1210 outside of the treatment chamber. The vent port 1214 may be located anywhere in fluid communication with the fluid circuit, including external connecting lines shown in FIG. 6. The catheter 1210 permits membrane degasification of the liquid drug solution during circulation or recirculation of the drug solution through the treatment chamber, a function not provided by the catheter 1110. During the purging process, or at any time air or gases are present in the lumen 95 proximate to the port 1214, the air or gases can be expelled via the membrane 90 while retaining liquid drug solution in the lumen 95. Membrane degasification of the liquid drug solution requires a pressure gradient across the membrane 90, which can be provided by pressurizing the liquid drug solution and/or by vacuating the external surface of the membrane 90. The vent port 1214 or another similar port may be incorporated into any of the catheters discussed herein.

The membrane 90 may comprise a biocompatible porous hydrophobic material such as, but not limited to polypropylene (PP), polytetrafluoroethylene (PTFE), polyvinylidene fluoride (PVDF), or ultra-high molecular weight polyethylene (UHMWPE). The membrane 90 may be adhered or welded to a variety of suitable catheter materials and may form a patch or cover over the egress port or may surround the entire catheter shaft proximate the egress port. The membrane 90 may selectively be applied over any of the ports in the catheter embodiments disclosed herein.

The following chemotherapeutic drugs are considered to be usable with the technology of the disclosure, but are merely given as examples, and not by way of limitation: vinblastine (VELBE), vinorelbine (NAVELBINE), irinotecan (CAMPTOSAR), paclitaxel (TAXOL), docetaxel (TAXOTERE), epirubicin (ELLENCE), doxorubicin (ADRIAMYCIN), capecitabine (XELODA), etoposide (ETOPOPHOS), topotecan (HYCAMTIN), pemetrexed (ALIMTA), carboplatin (PARAPLATIN), fluorouracil (ADRUCIL), gemcitabine (GEMZAR), oxaliplatin (ELOXATIN), cisplatin (PLATINOL), trastuzumab (HERCEPTIN), ramucirumab (CYRAMZA), and bevacizumab (AVASTIN).

Further examples of embodiments consistent with the present disclosure include those described in the following paragraphs.

An example includes a catheter for delivery of a drug to a target tissue area of an internal body organ of a patient, the catheter having an elongate flexible shaft and two longitudinally spaced-apart expandable members disposed about a catheter shaft distal region, the expandable members being transformable between a collapsed delivery configuration and an expanded configuration for sealing against a natural lumen extending through the target tissue area to form a closed treatment chamber defined between the two expandable members and the wall of the natural lumen, the catheter further having first and second drug-delivery lumens extending from a catheter proximal end to respective first and second ports disposed between the expandable members.

An additional example includes the features of the previous example, and further includes an orientation sensor mounted at the catheter shaft distal region.

An additional example includes the features of the previous examples, wherein the two expandable members respectively comprise two compliant balloons wherein each compliant balloon is inflatable to varying diameters, the catheter further having one or more inflation lumens extending from the catheter proximal end to the expandable members for inflating each of the compliant balloons either together or independently.

An additional example includes the features of the previous examples, and further includes a navigation camera disposed adjacent the distal region.

An additional example includes the features of the previous examples, and further includes two fiducial markers for referencing the respective locations of the two expandable members when the catheter is viewed using a medical imaging system or a navigation system.

An additional example includes the features of the previous examples, wherein the two longitudinally spaced-apart expandable members are configured for forming a closed treatment chamber within a lumen of a gastrointestinal tract, a female genital tract, a urinary tract, or a respiratory tract.

An additional example includes a catheter for local delivery of a drug to a target tissue area of an internal body organ of a patient, the catheter comprising: an elongate flexible shaft; first and second longitudinally spaced-apart expandable members disposed about a distal region of the flexible shaft, the expandable members each being transformable between a collapsed delivery configuration and an expanded configuration for sealing against the wall of a natural lumen extending through the target tissue area to form a closed treatment chamber defined between the first and second expandable members and the wall of the natural lumen; a liquid ingress lumen extending from a shaft proximal end to a liquid ingress port located between the expandable members; and a liquid egress lumen extending from a shaft proximal end to a liquid egress port located between the expandable members; wherein the functions of the ingress and egress ports are reversible such that either port can be a high point of the formed closed treatment chamber with respect to gravity.

An additional example includes the features of the previous examples, and further includes an orientation sensor mounted at the shaft distal region and operable to indicate to an operator the orientation of the shaft distal region with respect to gravity.

An additional example includes the features of the previous examples, wherein the orientation sensor is an accelerometer adapted to communicate with an electronic console exterior to the patient.

An additional example includes the features of the previous examples, wherein the liquid ingress port is located adjacent to the first expandable member and the liquid egress port is located adjacent to the second expandable member.

An additional example includes the features of the previous examples, wherein both the first and second expandable members are compliant balloons inflatable to varying diameters, the flexible shaft further having one or more inflation lumens configured for inflating the compliant balloons either simultaneously or independently.

An additional example includes the features of the previous examples, and further includes a navigation camera disposed adjacent the distal region.

An additional example includes the features of the previous examples, and further includes one or more fiducial markers for referencing the respective locations of the first and second expandable members when the catheter is viewed using a medical imaging system or a navigation system.

An additional example includes the features of the previous examples, wherein the first and second longitudinally spaced-apart expandable members are configured for forming a closed treatment chamber within a lumen of a gastrointestinal tract, a female genital tract, a urinary tract, or a respiratory tract.

An additional example includes the features of the previous examples, and further includes one or more electrodes disposed between the first and second longitudinally spaced-apart expandable members.

An additional example includes the features of the previous examples, wherein the electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a method for local delivery of a drug to a target tissue area of an internal body organ of a patient, the method comprising: inserting a distal region of an elongate flexible catheter shaft through a natural orifice into a natural lumen extending through the target tissue area; expanding two expandable members on the shaft distal region from a collapsed delivery configuration to an expanded configuration in sealing engagement with a wall of the natural lumen to thereby form a closed treatment chamber defined between the two expandable members and the wall of the natural lumen; and circulating a liquid drug solution for the duration of a treatment session through a closed fluid circuit that comprises the treatment chamber and two drug-delivery lumens that both extend through the flexible catheter shaft from two respective connecting ports exterior to the patient to two respective chamber ports disposed in the shaft distal region between the expandable members.

An additional example includes the features of the previous examples, and further includes: purging air from the treatment chamber before circulating the liquid drug solution, the purging including: determining the orientation of the shaft distal region with respect to gravity; repositioning the patient, if necessary, such that one of the chamber ports is located at a high point of the treatment chamber with respect to gravity and defining the port so located as a purge port; defining the other chamber port located below the purge port in the treatment chamber as a fill port; and filling the treatment chamber with the liquid drug solution through the fill port while permitting air to exit through the purge port.

An additional example includes the features of the previous examples, and further includes applying negative pressure to the drug-delivery lumen extending from the purge port to enhance purging of air from the treatment chamber.

An additional example includes the features of the previous examples, wherein the purge port is located adjacent to one of the expandable members.

An additional example includes the features of the previous examples, and further includes terminating the treatment session; and evacuating the treatment chamber of liquid drug solution after terminating the treatment session.

An additional example includes the features of the previous examples, and further includes: measuring a change in a drug concentration in the circulating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

An additional example includes the features of the previous examples, and further includes terminating the treatment session if the calculated amount of the drug dispensed from the treatment chamber equals or exceeds a predetermined maximum threshold amount.

An additional example includes the features of the previous examples, and further includes terminating the treatment session if the calculated amount of the drug dispensed from the treatment chamber is within a predetermined therapeutic window.

An additional example includes the features of the previous examples, and further includes measuring a drug concentration in the circulating drug solution during the treatment session; and terminating the treatment session if the measured drug concentration is equal to or less than a predetermined minimum threshold amount.

An additional example includes the features of the previous examples, wherein maximum and minimum drug dosage values define the therapeutic window and the drug dosage values are calculated based at least in part on a desired amount of the drug to be absorbed and an estimated surface area of the wall of the natural lumen in the treatment chamber.

An additional example includes the features of the previous examples, wherein the surface area of the luminal wall in the treatment chamber is estimated based at least in part on one or more of the following parameters: a known distance between the two expandable members; a diameter of at least one of the two expandable members; a distance from the natural orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients.

An additional example includes the features of the previous examples, wherein the diameter of at least one of the two expandable members is measured from a medical image or the at least one of the two expandable members is an inflatable elastic balloon and a diameter of the balloon is determined based at least in part on a volume used to inflate the balloon.

An additional example includes the features of the previous examples, and further includes: estimating the volume of the target tissue area based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

An additional example includes the features of the previous examples, wherein measuring a change in the drug concentration in the circulating drug solution is performed using an osmometer.

An additional example includes the features of the previous examples, wherein circulating the liquid drug solution achieves homogeneous concentration of the drug in the drug solution within in the treatment chamber.

An additional example includes the features of the previous examples, wherein transforming two expandable members further comprises adjusting a longitudinal distance between the expandable members such that the length of the closed treatment chamber corresponds with a length of the target tissue area.

An additional example includes the features of the previous examples, wherein circulating the liquid drug solution further comprises continuing to circulate the liquid drug solution until the drug has saturated the target tissue area and passed therethrough into the surrounding interstitial space or the proximate lymphatic system of the patient, all of which may act as a conduit or reservoir for the drug.

An additional example includes a method for local delivery of a drug to a target tissue area of an internal body organ of a patient, the method comprising: inserting a distal region of an elongate flexible catheter shaft through a natural orifice into a natural lumen extending through the target tissue area; transforming two expandable members on the distal region from a collapsed delivery configuration to an expanded configuration in sealing engagement with a wall of the natural lumen to thereby form a closed treatment chamber defined between the two expandable members and the wall of the natural lumen; and recirculating a liquid drug solution for the duration of a treatment session through a closed-loop fluid circuit that comprises the treatment chamber and two drug-delivery lumens that both extend through the catheter shaft from two respective connecting ports exterior to the patient to two respective chamber ports disposed in the shaft distal region between the expandable members.

An additional example includes the features of the previous examples, and further includes: purging air from the treatment chamber before recirculating the liquid drug solution, the purging including: determining the orientation of the distal region with respect to gravity; repositioning the patient, if necessary, such that a one of the chamber ports is located at a high point of the treatment chamber with respect to gravity and defining the port so located as a purge port; defining the other chamber port located below the purge port in the treatment chamber as a fill port; and filling the treatment chamber with the liquid drug solution through the fill port while permitting air to exit through the purge port.

An additional example includes the features of the previous examples, and further includes applying negative pressure to the drug-delivery lumen extending from the purge port to enhance purging of air from the treatment chamber.

An additional example includes the features of the previous examples, wherein the purge port is located adjacent to one of the expandable members.

An additional example includes the features of the previous examples, and further includes terminating the treatment session and evacuating the treatment chamber of liquid drug solution after terminating the treatment session.

An additional example includes the features of the previous examples, and further includes: measuring a change in a drug concentration in the recirculating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

An additional example includes the features of the previous examples, and further includes terminating the treatment session if the calculated amount of the drug dispensed from the treatment chamber equals or exceeds a predetermined maximum threshold amount.

An additional example includes the features of the previous examples, and further includes terminating the treatment session if the calculated amount of the drug dispensed from the treatment chamber is within a predetermined therapeutic window.

An additional example includes the features of the previous examples, and further includes measuring a drug concentration in the recirculating drug solution during the treatment session; and terminating the treatment session if the measured drug concentration is equal to or less than a predetermined minimum threshold amount.

An additional example includes the features of the previous examples, wherein maximum and minimum drug dosage values define the therapeutic window and the drug dosage values are calculated based at least in part on a desired amount of the drug to be absorbed and an estimated surface area of the wall of the natural lumen in the treatment chamber.

An additional example includes the features of the previous examples, wherein the surface area of the luminal wall in the treatment chamber is estimated based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients.

An additional example includes the features of the previous examples, wherein the diameter of at least one of the expandable members is measured from a medical image or the at least one of the expandable members is an inflatable elastic balloon and a diameter of the balloon is determined based at least in part on a volume used to inflate the balloon.

An additional example includes the features of the previous examples, and further includes: estimating the volume of the target tissue area based at least in part on one or more of the following parameters: a known distance between the two expandable members; a diameter of at least one of the two expandable members; a distance from the orifice of the natural lumen to one of the two expandable members; an analysis of current and/or previous medical images of the natural lumen extending through the target tissue area of the internal body organ of the patient; a liquid capacity of the treatment chamber measured when filling the treatment chamber before recirculating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

An additional example includes the features of the previous examples, wherein measuring a change in the drug concentration in the recirculating drug solution is performed using an osmometer.

An additional example includes the features of the previous examples, wherein the steps of recirculating a liquid drug solution, measuring a change in a drug concentration in the recirculating drug solution, and calculating the amount of the drug absorbed from the treatment chamber are performed by a system comprising a pump, an osmometer, and a control unit configured to operate the pump based at least in part on one or more inputs selected from elapsed time, instantaneous pressure in the closed-loop fluid circuit, amount of the drug solution added to the fluid circuit, instantaneous drug concentration of the drug solution occupying the closed-loop fluid circuit, and manual data entered by an operator.

An additional example includes the features of the previous examples, and further includes monitoring a fluid pressure in the closed-loop fluid circuit.

An additional example includes the features of the previous examples, and further includes maintaining the fluid pressure in the closed-loop fluid circuit within a predetermined pressure range.

An additional example includes the features of the previous examples, wherein the predetermined pressure range includes a positive pressure sufficient to enhance uptake of drug into the target tissue area.

An additional example includes the features of the previous examples, wherein if the monitored fluid pressure exceeds the predetermined pressure range, then a pumping pressure is reduced by a recirculating pump in the closed-loop fluid circuit.

An additional example includes the features of the previous examples, wherein if the monitored fluid pressure is below the predetermined pressure range, then a pumping pressure is increased by a recirculating pump in the closed-loop fluid circuit and/or additional drug solution or solvent is added to the closed-loop fluid circuit.

An additional example includes the features of the previous examples, and further includes terminating recirculation of the drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that one or both of the expandable members is not sufficiently sealing against the wall of the natural lumen.

An additional example includes the features of the previous examples, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

An additional example includes the features of the previous examples, and further includes flushing the drug solution from the closed-loop fluid circuit at the end of the treatment session.

An additional example includes the features of the previous examples, wherein recirculating the liquid drug solution further comprises pumping the liquid drug solution from a pump through one of two drug-delivery lumens to the treatment chamber while permitting the liquid drug solution to return from the treatment chamber to the pump via the other of the two drug-delivery lumens.

An additional example includes a method for local delivery of a liquid drug to a target tissue area surrounding a natural lumen extending through a female genital tract or a respiratory tract or a urinary tract or gastrointestinal tract of a patient, the method comprising: inserting a distal region of an elongate flexible catheter through a natural orifice into the natural lumen to a location proximate to the target tissue area; transforming an expandable member on the elongate flexible catheter from a collapsed delivery configuration to an expanded configuration that sealingly engages a wall of the natural lumen proximal to the target tissue area to thereby create a treatment chamber defined by the portion of the natural lumen distal of the expandable member; and circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member.

An additional example includes the features of the previous examples, wherein transforming an expandable member further comprises adjusting a length of the catheter region distal of the expandable member to correspond with a length of the target tissue area.

An additional example includes the features of the previous examples, wherein circulating a liquid drug solution comprises delivering a known liquid drug concentration with a known tissue permeability of the drug concentration at a selected flow rate for a selected period of time.

An additional example includes the features of the previous examples, wherein circulating a liquid drug solution further comprises pushing a liquid other than the liquid drug through the catheter drug-delivery lumen to force the liquid drug from the catheter drug-delivery lumen into the treatment chamber.

An additional example includes the features of the previous examples, wherein the two respective chamber ports in the catheter region distal of the expandable member are longitudinally spaced-apart.

An additional example includes the features of the previous examples, and further includes adjusting the distance that the chamber ports are spaced-apart to correspond with a length of the target tissue area.

An additional example includes the features of the previous examples, and further includes evacuating the treatment chamber before circulating a liquid drug solution.

An additional example includes the features of the previous examples, and further includes evacuating the treatment chamber of the liquid drug solution after terminating the treatment session.

An additional example includes the features of the previous examples, and further includes: measuring a change in a drug concentration in the circulating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

An additional example includes the features of the previous examples, and further includes terminating the treatment session if the calculated amount of the drug dispensed from the treatment chamber equals or exceeds a predetermined maximum threshold amount.

An additional example includes the features of the previous examples, and further includes terminating the treatment session if the calculated amount of the drug dispensed from the treatment chamber is within a predetermined therapeutic window.

An additional example includes the features of the previous examples, and further includes measuring a drug concentration in the circulating drug dose during the treatment session and terminating the treatment session if the measured drug concentration is equal to or less than a predetermined minimum threshold amount.

An additional example includes the features of the previous examples, wherein maximum and minimum drug dosage values define the therapeutic window and the drug dosage values are calculated before the drug solution is circulated based at least in part on a desired amount of the drug to be absorbed and an estimated surface area of the wall of the natural lumen in the treatment chamber.

An additional example includes the features of the previous examples, wherein the surface area of the luminal wall in the treatment chamber is estimated based at least in part on one or more of the following parameters: a diameter of the expandable member; a distance from the orifice of the natural lumen to the expandable member; a distance from the expandable member to the chamber port located most distally therefrom; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients.

An additional example includes the features of the previous examples, wherein the diameter of the expandable member is measured from a medical image or the expandable member is an inflatable elastic balloon and a diameter of the balloon is determined based at least in part on a volume of a fluid used to inflate the balloon.

An additional example includes the features of the previous examples, and further includes estimating the volume of the target tissue area based at least in part on one or more of the following parameters: a diameter of the expandable member; a distance from the orifice of the natural lumen to the expandable member; a distance from the expandable member to the chamber port located most distally therefrom; an analysis of current and/or previous medical images of the natural lumen extending through the target tissue area of the internal body organ of the patient; a liquid capacity of the treatment chamber measured when filling the treatment chamber before circulating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

An additional example includes the features of the previous examples, wherein measuring a change in the drug concentration in the circulating drug solution is performed using an osmometer.

An additional example includes the features of the previous examples, wherein circulating a liquid drug solution through a closed fluid circuit further comprises recirculating the liquid drug solution through a closed-loop fluid circuit and the steps of recirculating a liquid drug solution, measuring a change in a drug concentration in the recirculating liquid drug solution, and calculating the amount of the drug absorbed from the treatment chamber are performed by a system comprising a pump, an osmometer, and a control unit configured to operate the pump based at least in part on one or more inputs selected from elapsed time, instantaneous fluid pressure in the closed-loop fluid circuit, amount of the liquid drug solution added to the fluid circuit, instantaneous drug concentration of the liquid drug solution occupying the closed-loop fluid circuit, and manual data entered by an operator.

An additional example includes the features of the previous examples, and further includes monitoring a fluid pressure in the closed-loop fluid circuit.

An additional example includes the features of the previous examples, and further includes maintaining the fluid pressure in the closed-loop fluid circuit within a predetermined pressure range.

An additional example includes the features of the previous examples, wherein the predetermined pressure range includes a positive pressure sufficient to enhance uptake of drug into the target tissue area.

An additional example includes the features of the previous examples, wherein if the monitored fluid pressure exceeds the predetermined pressure range, then a pumping pressure is reduced by the pump in the closed-loop fluid circuit.

An additional example includes the features of the previous examples, wherein if the monitored fluid pressure is below the predetermined pressure range, then a pumping pressure is increased by the pump in the closed-loop fluid circuit and/or additional drug solution or solvent is added to the closed-loop fluid circuit.

An additional example includes the features of the previous examples, and further includes terminating recirculation of the liquid drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that one or both of the expandable members is not sufficiently sealing against the wall of the natural lumen.

An additional example includes the features of the previous examples, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

An additional example includes the features of the previous examples, and further includes flushing the liquid drug from the closed-loop fluid circuit at the end of the treatment session.

An additional example includes the features of the previous examples, wherein recirculating the liquid drug solution further comprises pumping the liquid drug solution from the pump through one of the two drug-delivery lumens to the treatment chamber while permitting the liquid drug solution to return from the treatment chamber to the pump via the other of the two drug-delivery lumens.

An additional example includes the features of the previous examples, wherein circulating the liquid drug solution achieves homogeneous concentration of the drug in the liquid drug solution within in the treatment chamber.

An additional example includes the features of the previous examples, wherein circulating the liquid drug solution further comprises continuing to circulate the liquid drug solution until the drug has saturated the target tissue area and passed therethrough into the surrounding interstitial space or the proximate lymphatic system of the patient, all of which may act as a conduit or reservoir for the drug.

An additional example includes the features of the previous examples, wherein the expandable member is an elastic balloon and predetermined expansion properties thereof comprise a predetermined relationship between inflation volume and diameter.

An additional example includes the features of the previous examples, wherein circulating the liquid drug solution further comprises maintaining a fluid pressure in the treatment chamber below a pre-determined maximum pressure.

An additional example includes a catheter for delivery of a drug to a target tissue area of an internal body organ of a patient, the catheter having an elongate flexible shaft and an expandable member disposed about a catheter shaft distal region, the expandable member being transformable between a collapsed delivery configuration and an expanded configuration for sealingly engaging a natural lumen extending through the target tissue area to form a closed treatment chamber defined by the portion of the natural lumen distal of the expandable member, the catheter further having first and second drug-delivery lumens extending from a catheter proximal end to respective first and second ports spaced-apart in the shaft region distal of the expandable members.

An additional example includes the features of the previous examples, wherein the proximal port is located adjacent to the expandable member.

An additional example includes the features of the previous examples, wherein the length between the first and second ports is selectively adjustable to correspond with a length of the target tissue area.

An additional example includes the features of the previous examples, wherein a length of the catheter region distal of the expandable member is selectively adjustable to correspond with a length of the target tissue area.

An additional example includes the features of the previous examples, and further includes an orientation sensor mounted at the catheter shaft distal region.

An additional example includes the features of the previous examples, wherein the expandable member comprises a compliant balloon inflatable to varying diameters, the catheter further having an inflation lumen extending from the catheter proximal end to the expandable member for inflation thereof.

An additional example includes the features of the previous examples, and further includes a navigation camera disposed adjacent the distal region.

An additional example includes the features of the previous examples, and further includes a fiducial marker for referencing the location of the expandable member when the catheter is viewed using an imaging system.

An additional example includes the features of the previous examples, wherein the expandable member is configured for forming a treatment chamber within a lumen of a gastrointestinal tract, a female genital tract, a urinary tract, or a respiratory tract.

An additional example includes a catheter for local delivery of a drug to a target tissue area of an internal body organ of a patient, the catheter comprising: an elongate flexible shaft; an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member; a liquid ingress lumen extending from a shaft proximal end to a liquid ingress port located distal of the expandable member; and a liquid egress lumen extending from a shaft proximal end to a liquid egress port located distal of the expandable member; wherein the functions of the ingress and egress ports are reversible such that either port can be a high point of the formed treatment chamber with respect to gravity.

An additional example includes the features of the previous examples, and further includes an orientation sensor mounted at the shaft distal region and operable to indicate to an operator the orientation of the shaft distal region with respect to gravity.

An additional example includes the features of the previous examples, wherein the orientation sensor is an accelerometer adapted to communicate with an electronic console exterior to the patient.

An additional example includes the features of the previous examples, wherein one of the liquid ingress port and the liquid egress port is located adjacent to the expandable member.

An additional example includes the features of the previous examples, wherein a length of the catheter region distal of the expandable member is selectively adjustable to correspond with a length of the target tissue area.

An additional example includes the features of the previous examples, wherein the expandable member is a compliant balloon inflatable to varying diameters, the shaft further having an inflation lumen configured for inflating the compliant balloon.

An additional example includes the features of the previous examples, and further includes a navigation camera disposed adjacent the distal region.

An additional example includes the features of the previous examples, and further includes a fiducial marker for referencing the location of the expandable member when the catheter is viewed using a medical imaging system or navigation system.

An additional example includes the features of the previous examples, wherein the expandable member is configured for forming a treatment chamber within a lumen of a gastrointestinal tract, a urinary tract, a female reproductive tract, or a respiratory tract.

An additional example includes the features of the previous examples, and further includes one or more spaced-apart electrodes disposed distally of the expandable member.

An additional example includes the features of the previous examples, wherein the electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a catheter for delivery of a drug to a target tissue area of a lung of a patient, the catheter having: an elongate flexible shaft and an expandable member disposed about a catheter shaft distal region, the expandable member being transformable between a collapsed delivery configuration and an expanded configuration for sealingly engaging a bronchus extending through the target tissue area to form a closed treatment chamber defined by the portion of the bronchus distal of the expandable member; first and second drug-delivery lumens extending from a catheter proximal end to respective first and second ports spaced-apart in the shaft region distal of the expandable member; an inflatable cuff disposed about the catheter shaft proximally of the expandable member and being transformable between a collapsed delivery configuration and an expanded configuration for sealingly engaging a trachea at a location above a tracheal carina of the patient; one or more ventilation ports located between the cuff and the expandable member; and a ventilation lumen extending from a catheter proximal end to the one or more ventilation ports.

An additional example includes the features of the previous examples, wherein the first port is located adjacent to the expandable member.

An additional example includes the features of the previous examples, wherein the length between the first and second ports is selectively adjustable to correspond with a length of the target tissue area.

An additional example includes the features of the previous examples, wherein a length of the catheter region distal of the expandable member is selectively adjustable to correspond with a length of the target tissue area.

An additional example includes the features of the previous examples, and further includes an orientation sensor, an accelerometer, or an IMU mounted at the catheter shaft distal region.

An additional example includes the features of the previous examples, and further includes a navigation camera disposed adjacent the distal region.

An additional example includes the features of the previous examples, and further includes at least one port configured for membrane degasification of a liquid drug solution carried by the first and second drug-delivery lumens.

An additional example includes the features of the previous examples, wherein the at least one membrane degasification port comprises a membrane that is gas-permeable but is not liquid permeable; and wherein the at least one membrane degasification port is one of the first and second ports distal of the expandable member or the at least one membrane degasification port is located proximal to the expandable member.

An additional example includes a catheter for local delivery of a drug to a target tissue area of a lung of a patient, the catheter comprising: an elongate flexible shaft; an expandable member disposed about a distal region of the elongate flexible shaft and being transformable between a collapsed delivery configuration and an expanded configuration for sealing against the wall of a bronchus extending through the target tissue area to form a treatment chamber defined by the wall of the bronchus distal of the expandable member; a liquid ingress lumen extending from a shaft proximal end to a liquid ingress port located distal of the expandable member; and a liquid egress lumen extending from a shaft proximal end to a liquid egress port located distal of the expandable member; and an inflatable cuff disposed about the catheter shaft proximally of the expandable member and being transformable between a collapsed delivery configuration and an expanded configuration for sealingly engaging a trachea of the patient; one or more ventilation ports located between the cuff and the expandable member; and a ventilation lumen extending from the catheter proximal end to the one or more ventilation ports; wherein the functions of the ingress and egress ports are reversible such that either port can be a high point of the formed treatment chamber with respect to gravity.

An additional example includes the features of the previous examples, and further includes an orientation sensor mounted at the distal region and operable to indicate to an operator the orientation of the distal region with respect to gravity.

An additional example includes the features of the previous examples, wherein the orientation sensor is an accelerometer or an IMU adapted to communicate with an electronic console exterior to the patient.

An additional example includes the features of the previous examples, wherein one of the liquid ingress port and the liquid egress port is located adjacent to the expandable member.

An additional example includes the features of the previous examples, wherein a length of the catheter region distal of the expandable member is selectively adjustable to correspond with a length of the target tissue area.

An additional example includes the features of the previous examples, and further includes a navigation camera disposed adjacent the distal region.

An additional example includes the features of the previous examples, and further includes at least one port configured for membrane degasification of a liquid drug solution carried by the ingress and egress lumens.

An additional example includes the features of the previous examples, wherein the at least one membrane degasification port comprises a membrane that is gas-permeable but is not liquid permeable; and wherein the at least one membrane degasification port is the egress port or the at least one membrane degasification port is located proximal to the expandable member.

An additional example includes the features of the previous examples, and further includes one or more spaced-apart electrodes disposed distally of the expandable member.

An additional example includes the features of the previous examples, wherein the spaced-apart electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a method for local delivery of a liquid drug solution to a target lung tissue area surrounding a bronchus of a patient, the method comprising: inserting a distal region of an elongate flexible catheter through a natural orifice into a first bronchus to a location proximate to the target tissue area; transforming an expandable member on the elongate flexible catheter from a collapsed delivery configuration to an expanded configuration that sealingly engages a wall of the first bronchus proximal to the target tissue area to thereby create a treatment chamber defined by the portion of the first bronchus distal of the expandable member; transforming an inflatable cuff on the elongate flexible catheter from a collapsed delivery configuration to an expanded configuration that sealingly engages a tracheal wall at a location above a tracheal carina of the patient; circulating the liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member; and ventilating a second bronchus opposite the first bronchus through a ventilation lumen extending through the catheter shaft from a respective connecting port exterior to the patient to one or more ventilation ports disposed in the shaft between the inflatable cuff and the expandable member.

An additional example includes the features of the previous examples, wherein transforming an expandable member further comprises adjusting a length of the catheter region distal of the expandable member to correspond with a length of the target tissue area.

An additional example includes the features of the previous examples, wherein circulating a liquid drug solution comprises delivering a known liquid drug concentration with a known tissue permeability of the drug concentration at a selected flow rate for a selected period of time.

An additional example includes the features of the previous examples, wherein circulating the liquid drug solution further comprises pushing a liquid other than the liquid drug solution through the catheter drug-delivery lumen to force the liquid drug solution from the catheter drug-delivery lumen into the treatment chamber.

An additional example includes the features of the previous examples, wherein the two respective chamber ports in the catheter region distal of the expandable member are longitudinally spaced-apart.

An additional example includes the features of the previous examples, and further includes evacuating the treatment chamber before circulating the liquid drug solution.

An additional example includes the features of the previous examples, and further includes degasifying liquid drug in the closed fluid circuit via at least one degasification membrane.

An additional example includes the features of the previous examples, wherein the at least one membrane degasification port is associated with one of the chamber ports, or the at least one membrane degasification port is located proximal to the expandable member.

An additional example includes the features of the previous examples, and further includes: measuring a change in a drug concentration in the circulating liquid drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

An additional example includes the features of the previous examples, and further includes terminating the treatment session if the calculated amount of the drug dispensed from the treatment chamber equals or exceeds a predetermined maximum threshold amount.

An additional example includes the features of the previous examples, and further includes terminating the treatment session if the calculated amount of the drug dispensed from the treatment chamber is within a predetermined therapeutic window.

An additional example includes the features of the previous examples, and further includes measuring a drug concentration in the circulating drug dose and/or in the patient's circulating blood during the treatment session and terminating the treatment session if the measured drug concentration in the circulating drug dose is equal to or less than a predetermined minimum threshold amount for the circulating drug dose or if the measured drug concentration in the blood is equal to or greater than a predetermined minimum threshold amount in the patient's blood.

An additional example includes the features of the previous examples, wherein the maximum and minimum drug dosage values define the therapeutic window and the drug dosage values are calculated before the liquid drug solution is circulated based at least in part on a desired amount of the drug to be absorbed and an estimated surface area of the wall of the first bronchus in the treatment chamber.

An additional example includes the features of the previous examples, wherein the surface area of the first bronchus wall in the treatment chamber is estimated based at least in part on one or more of the following parameters: a diameter of the expandable member; a distance from the orifice of the natural lumen to the expandable member; a distance from the expandable member to the chamber port located most distally therefrom; an analysis of current and/or previous medical images of the first bronchus extending through the target tissue area of the lung of the patient; a liquid capacity of the treatment chamber measured when filling the treatment chamber before circulating the liquid drug solution; and a statistical analysis of historical data regarding physical dimensions of similar bronchi extending through similar target tissue areas for a known population of patients.

An additional example includes the features of the previous examples, wherein the diameter of the expandable member is measured from a medical image or the expandable member is an inflatable elastic balloon and a diameter of the balloon is determined based at least in part on a volume of a fluid used to inflate the balloon.

An additional example includes the features of the previous examples, and further includes: estimating the volume of the target tissue area based at least in part on one or more of the following parameters: a diameter of the expandable member; a distance from the orifice of the bronchus to the expandable member; a distance from the expandable member to the chamber port located most distally therefrom; an analysis of current and/or previous medical images of the bronchus extending through the target lung tissue area of the patient; a liquid capacity of the treatment chamber measured when filling the treatment chamber before circulating the liquid drug solution; and a statistical analysis of historical data regarding physical dimensions of similar bronchi extending through similar target lung tissue areas for a known population of patients; and calculating a desired amount of the circulating liquid drug solution to be delivered based at least in part on one or more inputs selected from the estimated surface area of the treatment chamber, the estimated volume of the target lung tissue area, and a known rate of transfer of the drug through the wall of the bronchus and into the target lung tissue area.

An additional example includes the features of the previous examples, wherein measuring a change in the drug concentration in the circulating liquid drug solution is performed using an osmometer.

An additional example includes the features of the previous examples, wherein circulating the liquid drug solution through a closed fluid circuit further comprises recirculating the liquid drug solution through a closed-loop fluid circuit and the steps of recirculating the liquid drug solution, measuring a change in a drug concentration in the recirculating liquid drug solution, and calculating the amount of the drug absorbed from the treatment chamber are performed by a system comprising a pump, an osmometer, and a control unit configured to operate the pump based at least in part on one or more inputs selected from elapsed time, instantaneous fluid pressure in the closed-loop fluid circuit, amount of the liquid drug solution added to the fluid circuit, instantaneous drug concentration of the liquid drug solution occupying the closed-loop fluid circuit, and manual data entered by an operator.

An additional example includes the features of the previous examples, and further includes monitoring a fluid pressure in the closed-loop fluid circuit.

An additional example includes the features of the previous examples, and further includes maintaining the fluid pressure in the closed-loop fluid circuit within a predetermined pressure range.

An additional example includes the features of the previous examples, wherein the predetermined pressure range includes a positive pressure sufficient to enhance uptake of drug into the target lung tissue area.

An additional example includes the features of the previous examples, wherein if the monitored fluid pressure exceeds the predetermined pressure range, then a pumping pressure is reduced by the pump in the closed-loop fluid circuit.

An additional example includes the features of the previous examples, wherein if the monitored fluid pressure is below the predetermined pressure range, then a pumping pressure is increased by the pump in the closed-loop fluid circuit and/or additional liquid drug solution or solvent is added to the closed-loop fluid circuit.

An additional example includes the features of the previous examples, and further includes terminating the recirculating of the liquid drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that the expandable member is not sufficiently sealing against the wall of the bronchus.

An additional example includes the features of the previous examples, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

An additional example includes the features of the previous examples, and further includes flushing the liquid drug solution from the closed-loop fluid circuit at the end of the treatment session.

An additional example includes the features of the previous examples, wherein recirculating the liquid drug solution further comprises pumping the liquid drug solution from the pump through one of the two drug-delivery lumens to the treatment chamber while permitting the liquid drug to return from the treatment chamber to the pump via the other of the two drug-delivery lumens.

An additional example includes the features of the previous examples, wherein circulating the liquid drug solution achieves homogeneous concentration of the drug in the liquid drug solution within in the treatment chamber.

An additional example includes the features of the previous examples, wherein circulating the liquid drug solution further comprises continuing to circulate the liquid drug solution until the drug has saturated the target lung tissue area and passed therethrough into the surrounding interstitial space or the proximate lymphatic system of the patient, all of which may act as a conduit or reservoir for the drug.

An additional example includes the features of the previous examples, wherein the expandable member is an elastic balloon and predetermined expansion properties thereof comprise a predetermined relationship between inflation volume and diameter.

An additional example includes the features of the previous examples, wherein circulating the liquid drug solution further comprises maintaining a fluid pressure in the treatment chamber below a pre-determined maximum pressure.

An additional example includes a catheter for bilateral local delivery of a drug to target tissue areas of both lungs of a patient, the catheter comprising: an elongate bifurcated flexible shaft; a first expandable member disposed about a first distal branch of the flexible shaft and being transformable between a collapsed delivery configuration and an expanded configuration for sealing against the wall of a first bronchus extending through the first target tissue area to form a treatment chamber defined by the wall of the first bronchus distal of the first expandable member; a first liquid ingress lumen extending from a shaft proximal end to a first liquid ingress port located distal of the first expandable member; and a first liquid egress lumen extending from a shaft proximal end to a first liquid egress port located distal of the first expandable member; wherein the functions of the first ingress and egress ports are reversible such that either port can be a high point of the formed treatment chamber with respect to gravity; a second expandable member disposed about a second distal branch of the flexible shaft and being transformable between a collapsed delivery configuration and an expanded configuration for sealing against the wall of a second bronchus extending through the second target tissue area to form a treatment chamber defined by the wall of the second bronchus distal of the second expandable member; a second liquid ingress lumen extending from a shaft proximal end to a second liquid ingress port located distal of the second expandable member; and a second liquid egress lumen extending from a shaft proximal end to a second liquid egress port located distal of the second expandable member; wherein the functions of the second ingress and egress ports are reversible such that either port can be a high point of the formed treatment chamber with respect to gravity.

An additional example includes the features of the previous examples, and further includes one or more orientation sensors mounted at the first and/or second shaft distal branch and operable to indicate to an operator the orientation of the respective shaft distal region with respect to gravity.

An additional example includes the features of the previous examples, wherein the one or more orientation sensors are accelerometers and/or IMUS adapted to communicate with an electronic console exterior to the patient.

An additional example includes the features of the previous examples, wherein the first liquid ingress port is located adjacent to the first expandable member and the first liquid egress port is spaced distally of the first liquid egress port and the second liquid ingress port is located adjacent to the second expandable member and the second liquid egress port is spaced distally of the second liquid egress port.

An additional example includes the features of the previous examples, and further includes one or more navigation cameras disposed adjacent the first and/or the second distal branches.

An additional example includes the features of the previous examples, and further includes at least one port configured for membrane degasification of a liquid drug solution carried by either the first or second liquid ingress or egress lumens.

An additional example includes the features of the previous examples, wherein the at least one membrane degasification port comprises a membrane that is gas-permeable but is not liquid permeable and wherein the at least one membrane degasification port is one of the first or second liquid ingress or egress ports or the at least one membrane degasification port is located proximal to the first or second expandable member.

An additional example includes the features of the previous examples, and further includes one or more electrodes disposed distally of each of the first and second expandable members.

An additional example includes the features of the previous examples, wherein the electrodes are configured and located to provide an impedance indication when liquid reaches the high point of each of the formed treatment chambers with respect to gravity.

An additional example includes the features of the previous examples, wherein the electrodes are configured and located to provide an impedance indication of a concentration of the drug in the liquid drug solution.

An additional example includes a method for bilateral local delivery of a drug to target tissue areas of both lungs of a patient, the method comprising: inserting a distal region of an elongate bifurcated flexible catheter through a natural orifice such that a first distal catheter branch extends into a first bronchus to a location proximate to a first target tissue area and a second distal catheter branch extends into a second bronchus to a location proximate to a second target tissue area; transforming an expandable member on the first branch from a collapsed delivery configuration to an expanded configuration that sealingly engages a wall of the first bronchus proximal to the first target tissue area to thereby create a first treatment chamber defined by the portion of the first bronchus distal of the first expandable member; transforming an expandable member on the second branch from a collapsed delivery configuration to an expanded configuration that sealingly engages a wall of the second bronchus proximal to the second target tissue area to thereby create a second treatment chamber defined by the portion of the second bronchus distal of the second expandable member; circulating a liquid drug solution for the duration of a treatment session through a first closed fluid circuit that comprises the first treatment chamber and two drug-delivery lumens that both extend through the catheter shaft from two respective connecting ports exterior to the patient to two respective chamber ports disposed in the first shaft region distal of the first expandable member; and circulating the liquid drug solution for the duration of the treatment session through a second closed fluid circuit that comprises the second treatment chamber and two drug-delivery lumens that both extend through the catheter shaft from two respective connecting ports exterior to the patient to two respective chamber ports disposed in the second shaft region distal of the second expandable member.

An additional example includes the features of the previous examples, and further includes: purging air from the first and or second treatment chambers before circulating the liquid drug solution, the purging comprising: determining the orientation of the respective distal catheter branch with respect to gravity; repositioning the patient, if necessary, such that one of the chamber ports is located at a high point of the respective treatment chamber with respect to gravity and defining the port so located as a purge port; defining the other chamber port of the respective treatment chamber located below the purge port in the treatment chamber as a fill port; and filling the respective treatment chamber with the liquid drug solution through the fill port while permitting air to exit through the purge port.

An additional example includes the features of the previous examples, and further includes applying negative pressure to the drug-delivery lumen extending from the defined purge port to enhance purging of air from the treatment chamber.

An additional example includes the features of the previous examples, wherein the defined purge port is located adjacent to one of the expandable members.

An additional example includes a method for local delivery of a liquid drug to a target tissue area surrounding a natural lumen extending through a respiratory tract of a patient, the method comprising: inserting a distal region of an elongate flexible catheter through a natural orifice into a first bronchus of the patient to a location proximate to the target tissue area; inserting an endotracheal tube through the natural orifice into the trachea of the patient; transforming an inflatable cuff on the endotracheal tube from a collapsed delivery configuration to an expanded configuration that sealingly engages the catheter and a tracheal wall at a location above a tracheal carina of the patient; transforming an expandable member on the catheter from a collapsed delivery configuration to an expanded configuration that sealingly engages a wall of the first bronchus proximal to the target tissue area to thereby create a treatment chamber defined by the portion of the first bronchus distal of the expandable member; ventilating a second bronchus opposite the first bronchus through the endotracheal tube; and circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member.

An additional example includes the features of the previous examples, wherein transforming an expandable member further comprises adjusting a length of the catheter region distal of the expandable member to correspond with a length of the target tissue area.

An additional example includes the features of the previous examples, wherein circulating the liquid drug solution comprises delivering a known liquid drug concentration with a known tissue permeability of the drug concentration at a selected flow rate for a selected period of time.

An additional example includes the features of the previous examples, wherein circulating the liquid drug solution further comprises pushing a liquid other than the liquid drug solution through the catheter drug-delivery lumen to force the liquid drug from the catheter drug-delivery lumen into the treatment chamber.

An additional example includes the features of the previous examples, wherein the two respective chamber ports in the catheter region distal of the expandable member are longitudinally spaced-apart.

An additional example includes the features of the previous examples, and further includes evacuating the treatment chamber before circulating a liquid drug solution.

An additional example includes the features of the previous examples, and further includes degasifying liquid drug in the closed fluid circuit via at least one degasification membrane.

An additional example includes the features of the previous examples, wherein the at least one membrane degasification port is associated with one of the chamber ports, or the at least one membrane degasification port is located proximal to the expandable member.

An additional example includes a catheter for local delivery of a drug to a target tissue area of an internal body organ of a patient, the catheter comprising: an elongate flexible shaft; an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member; a liquid ingress lumen extending from a shaft proximal end to a liquid ingress port located distal to the expandable member; and an egress lumen extending proximally through the flexible shaft from an egress port located distal to the expandable members; wherein the egress port is covered by a membrane that is permeable by gases but not permeable by a liquid containing the drug.

An additional example includes the features of the previous examples, wherein the egress lumen terminates proximally in an exhaust port disposed proximal to both of the expandable member.

An additional example includes the features of the previous examples, wherein the egress port is located adjacent to the expandable member to facilitate the egress port being located at a high point of the formed treatment chamber with respect to gravity.

An additional example includes the features of the previous examples, and further includes an orientation sensor mounted at the shaft distal region and operable to indicate to an operator the orientation of the shaft distal region with respect to gravity.

An additional example includes the features of the previous examples, wherein the orientation sensor is an accelerometer or an IMU adapted to communicate with an electronic console exterior to the patient.

An additional example includes the features of the previous examples, wherein the egress port is located adjacent to the expandable member.

An additional example includes the features of the previous examples, wherein the expandable member is a compliant balloon inflatable to varying diameters, the shaft further having an inflation lumen configured for inflating the compliant balloon.

An additional example includes the features of the previous examples, and further includes a navigation camera disposed adjacent the distal region.

An additional example includes the features of the previous examples, and further includes a fiducial marker for referencing the location of the expandable member when the catheter is viewed using a medical imaging system or a navigation system.

An additional example includes the features of the previous examples, wherein the expandable member is configured for forming a closed treatment chamber within a lumen of a gastrointestinal tract, a female genital tract, a urinary tract, or a respiratory tract.

An additional example includes the features of the previous examples, and further includes one or more electrodes disposed distally of the expandable member.

An additional example includes the features of the previous examples, wherein the electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a method for local delivery of a drug to a target tissue area of an internal body organ of a patient, the method comprising: inserting a distal region of an elongate flexible catheter shaft through a natural orifice into a natural lumen extending through the target tissue area; transforming an expandable member on the shaft distal region from a collapsed delivery configuration to an expanded configuration in sealing engagement with a wall of the natural lumen to thereby form a treatment chamber defined by the portion of the natural lumen distal of the expandable member; purging air from the treatment chamber, the purging comprising: determining the orientation of the shaft distal region with respect to gravity; repositioning the patient, if necessary, such that a purge port is located at a highpoint of the treatment chamber with respect to gravity; and filling the treatment chamber with the liquid drug solution through a fill port below the purge port while permitting air to exit the treatment chamber through a porous membrane at the purge port until the porous membrane blocks passage of the liquid drug solution through the purge port; and holding the liquid drug solution in the treatment chamber for the duration of a treatment session.

An additional example includes the features of the previous examples, and further includes applying negative pressure to the drug-delivery lumen extending from the purge port to enhance purging of air from the treatment chamber.

An additional example includes the features of the previous examples, wherein the purge port is located adjacent to the expandable member.

An additional example includes the features of the previous examples, wherein the air exiting the treatment chamber through the porous membrane at the purge port is exhausted from the catheter via an exhaust port located proximal to the expandable member.

An additional example includes the features of the previous examples, wherein the air exiting the treatment chamber through the porous membrane at the purge port is exhausted from a portion of the catheter located outside of the patient's body.

An additional example includes the features of the previous examples, and further includes terminating the treatment session and evacuating the treatment chamber of a liquid drug solution after terminating the treatment session.

An additional example includes the features of the previous examples, and further includes measuring a drug concentration in the patient's circulating blood during the treatment session; and terminating the treatment session if the measured drug concentration in the blood is equal to or greater than a predetermined minimum threshold amount in the patient's blood.

An additional example includes a catheter for delivery of a drug to a target tissue area of a lung of a patient, the catheter having: an elongate flexible shaft and an expandable member disposed about a catheter shaft distal region, the expandable member being transformable between a collapsed delivery configuration and an expanded configuration for sealingly engaging a bronchus extending through the target tissue area to form a closed treatment chamber defined by the portion of the bronchus distal of the expandable member; first and second drug-delivery lumens extending from a catheter proximal end to respective first and second ports spaced-apart in the shaft region distal of the expandable member; an inflatable cuff disposed about the flexible shaft proximally of the expandable member and being transformable between a collapsed delivery configuration and an expanded configuration for sealingly engaging a trachea at a location above a tracheal carina of the patient; one or more ventilation ports located between the cuff and the expandable member; and a ventilation lumen extending from a catheter proximal end to the one or more ventilation ports.

An additional example includes the features of the previous examples, wherein the proximal port is located adjacent to the expandable member.

An additional example includes the features of the previous examples, wherein the length between the first and second ports is selectively adjustable to correspond with a length of the target tissue area.

An additional example includes the features of the previous examples, wherein a length of the catheter region distal of the expandable member is selectively adjustable to correspond with a length of the target tissue area.

An additional example includes the features of the previous examples, and further includes an orientation sensor, an accelerometer, or an IMU mounted at the catheter shaft distal region.

An additional example includes the features of the previous examples, and further includes a navigation camera disposed adjacent the distal region.

An additional example includes the features of the previous examples, and further includes at least one port configured for membrane degasification of the liquid drug solution carried by the first and second drug-delivery lumens.

An additional example includes the features of the previous examples, wherein the at least one membrane degasification port comprises a membrane that is gas-permeable but is not liquid permeable; and wherein the at least one membrane degasification port is one of the first and second ports distal of the expandable member or the at least one membrane degasification port is located proximal to the expandable member.

An additional example includes a catheter for local delivery of a drug to a target tissue area of a lung of a patient, the catheter comprising: an elongate flexible shaft; an expandable member disposed about a distal region of the flexible shaft and being transformable between a collapsed delivery configuration and an expanded configuration for sealing against the wall of a bronchus extending through the target tissue area to form a treatment chamber defined by the wall of the bronchus distal of the expandable member; a liquid ingress lumen extending from a shaft proximal end to a liquid ingress port located distal of the expandable member; and a liquid egress lumen extending from a shaft proximal end to a liquid egress port located distal of the expandable member; and an inflatable cuff disposed about the flexible shaft proximally of the expandable member and being transformable between a collapsed delivery configuration and an expanded configuration for sealingly engaging a trachea of the patient; one or more ventilation ports located between the cuff and the expandable member; and a ventilation lumen extending from a catheter proximal end to the one or more ventilation ports; wherein the functions of the ingress and egress ports are reversible such that either port can be a high point of the formed treatment chamber with respect to gravity.

An additional example includes the features of the previous examples, and further includes an orientation sensor mounted at the shaft distal region and operable to indicate to an operator the orientation of the shaft distal region with respect to gravity.

An additional example includes the features of the previous examples, wherein the orientation sensor is an accelerometer or an IMU adapted to communicate with an electronic console exterior to the patient.

An additional example includes the features of the previous examples, wherein one of the liquid ingress port and the liquid egress port is located adjacent to the expandable member.

An additional example includes the features of the previous examples, wherein a length of the catheter region distal of the expandable member is selectively adjustable to correspond with a length of the target tissue area.

An additional example includes the features of the previous examples, and further includes a navigation camera disposed adjacent the distal region.

An additional example includes the features of the previous examples, and further includes at least one port configured for membrane degasification of a liquid drug solution carried by the ingress and egress lumens.

An additional example includes the features of the previous examples, wherein the at least one membrane degasification port comprises a membrane that is gas-permeable but is not liquid permeable; and wherein the at least one membrane degasification port is the egress port or the at least one membrane degasification port is located proximal to the expandable member.

An additional example includes the features of the previous examples, and further includes one or more spaced-apart electrodes disposed distally of the expandable member.

An additional example includes the features of the previous examples, wherein the electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a method for local delivery of a liquid drug solution to a target lung tissue area surrounding a bronchus of a patient, the method comprising: inserting a distal region of an elongate flexible catheter through a natural orifice into a first bronchus to a location proximate to the target tissue area; transforming an expandable member on the catheter from a collapsed delivery configuration to an expanded configuration that sealingly engages a wall of the first bronchus proximal to the target tissue area to thereby create a treatment chamber defined by the portion of the first bronchus distal of the expandable member; transforming an inflatable cuff on the catheter from a collapsed delivery configuration to an expanded configuration that sealingly engages a tracheal wall at a location above a tracheal carina of the patient; circulating the liquid drug solution for the duration of a treatment session through a closed fluid circuit that comprises the treatment chamber and two drug-delivery lumens that both extend through the flexible shaft from two respective connecting ports exterior to the patient to two respective chamber ports disposed in the shaft region distal of the expandable member; and ventilating a second bronchus opposite the first bronchus through a ventilation lumen extending through the flexible shaft from a respective connecting port exterior to the patient to one or more ventilation ports disposed in the shaft between the inflatable cuff and the expandable member.

An additional example includes the features of the previous examples, wherein transforming an expandable member further comprises adjusting a length of the catheter region distal of the expandable member to correspond with a length of the target tissue area.

An additional example includes the features of the previous examples, wherein circulating the liquid drug solution comprises delivering a known liquid drug concentration with a known tissue permeability of the drug concentration at a selected flow rate for a selected period of time.

An additional example includes the features of the previous examples, wherein circulating the liquid drug solution further comprises pushing a liquid other than the liquid drug solution through the catheter drug-delivery lumen to force the liquid drug from the catheter drug-delivery lumen into the treatment chamber.

An additional example includes the features of the previous examples, wherein the two respective chamber ports in the catheter region distal of the expandable member are longitudinally spaced-apart.

An additional example includes the features of the previous examples, and further includes evacuating the treatment chamber before circulating the liquid drug solution.

An additional example includes the features of the previous examples, and further includes degasifying liquid drug in the closed fluid circuit via at least one degasification membrane.

An additional example includes the features of the previous examples, wherein the at least one membrane degasification port is associated with one of the chamber ports, or the at least one membrane degasification port is located proximal to the expandable member.

An additional example includes the features of the previous examples, and further includes: measuring a change in a drug concentration in the circulating drug solution over at least a portion of the treatment session; measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

An additional example includes the features of the previous examples, and further includes terminating the treatment session if the calculated amount of the drug dispensed from the treatment chamber equals or exceeds a predetermined maximum threshold amount.

An additional example includes the features of the previous examples, and further includes terminating the treatment session if the calculated amount of the drug dispensed from the treatment chamber is within a predetermined therapeutic window.

An additional example includes the features of the previous examples, and further includes measuring a drug concentration in the circulating liquid drug solution and/or in the patient's circulating blood during the treatment session; and terminating the treatment session if the measured drug concentration in the circulating liquid drug solution is equal to or less than a predetermined minimum threshold amount for the circulating liquid drug solution or if the measured drug concentration in the blood is equal to or greater than a predetermined minimum threshold amount in the patient's blood.

An additional example includes the features of the previous examples, wherein the maximum and minimum drug dosage values define the therapeutic window and the drug dosage values are calculated before the liquid drug solution is circulated based at least in part on a desired amount of the drug to be absorbed and an estimated surface area of the wall of the first bronchus in the treatment chamber.

An additional example includes the features of the previous examples, wherein the surface area of the first bronchus wall in the treatment chamber is estimated based at least in part on one or more of the following parameters: a diameter of the expandable member; a distance from the orifice of the natural lumen to the expandable member; a distance from the expandable member to the chamber port located most distally therefrom; an analysis of current and/or previous medical images of the first bronchus extending through the target tissue area of the lung of the patient; a liquid capacity of the treatment chamber measured when filling the treatment chamber before circulating the liquid drug solution; and a statistical analysis of historical data regarding physical dimensions of similar bronchi extending through similar target tissue areas for a known population of patients.

An additional example includes the features of the previous examples, wherein the diameter of the expandable member is measured from a medical image or the expandable member is an inflatable elastic balloon and a diameter of the balloon is determined based at least in part on a volume of a fluid used to inflate the balloon.

An additional example includes the features of the previous examples, and further includes estimating the volume of the target tissue area based at least in part on one or more of the following parameters: a diameter of the expandable member; a distance from the orifice of the bronchus to the expandable member; a distance from the expandable member to the chamber port located most distally therefrom; an analysis of current and/or previous medical images of the bronchus extending through the target lung tissue area of the patient; a liquid capacity of the treatment chamber measured when filling the treatment chamber before circulating the liquid drug solution; and a statistical analysis of historical data regarding physical dimensions of similar bronchi extending through similar target lung tissue areas for a known population of patients; and calculating a desired amount of the circulating liquid drug to be delivered based at least in part on one or more inputs selected from the estimated surface area of the treatment chamber, the estimated volume of the target lung tissue area, and a known rate of transfer of the drug through the wall of the bronchus and into the target lung tissue area.

An additional example includes the features of the previous examples, wherein measuring a change in the drug concentration in the circulating liquid drug solution is performed using an osmometer.

An additional example includes the features of the previous examples, wherein circulating the liquid drug solution through a closed fluid circuit further comprises recirculating the liquid drug solution through a closed-loop fluid circuit and the steps of recirculating the liquid drug solution, measuring a change in a drug concentration in the recirculating drug solution, and calculating the amount of the drug absorbed from the treatment chamber are performed by a system comprising a pump, an osmometer, and a control unit configured to operate the pump based at least in part on one or more inputs selected from elapsed time, instantaneous fluid pressure in the closed-loop fluid circuit, amount of the drug solution added to the fluid circuit, instantaneous drug concentration of the drug solution occupying the closed-loop fluid circuit, and manual data entered by an operator. An additional example includes the features of the previous examples, and further includes monitoring a fluid pressure in the closed-loop fluid circuit.

An additional example includes the features of the previous examples, and further includes maintaining the fluid pressure in the closed-loop fluid circuit within a predetermined pressure range.

An additional example includes the features of the previous examples, wherein the predetermined pressure range includes a positive pressure sufficient to enhance uptake of drug into the target lung tissue area.

An additional example includes the features of the previous examples, wherein if the monitored fluid pressure exceeds the predetermined pressure range, then a pumping pressure is reduced by the pump in the closed-loop fluid circuit.

An additional example includes the features of the previous examples, wherein if the monitored fluid pressure is below the predetermined pressure range, then a pumping pressure is increased by the pump in the closed-loop fluid circuit and/or additional drug solution or solvent is added to the closed-loop fluid circuit.

An additional example includes the features of the previous examples, and further includes terminating the recirculating of a drug solution if a leak in the treatment chamber is indicated by one or more of the following conditions: the fluid pressure in the closed-loop fluid circuit drops below a predetermined minimum pressure; a calculated rate of pressure change in the closed-loop fluid exceeds a predetermined rate of change, and a medical image of the patient shows that the expandable member is not sufficiently sealing against the wall of the bronchus.

An additional example includes the features of the previous examples, wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

An additional example includes the features of the previous examples, and further includes flushing the liquid drug solution from the closed-loop fluid circuit at the end of the treatment session.

An additional example includes the features of the previous examples, wherein recirculating the liquid drug solution further comprises pumping the liquid drug solution from the pump through one of the two drug-delivery lumens to the treatment chamber while permitting the liquid drug solution to return from the treatment chamber to the pump via the other of the two drug-delivery lumens.

An additional example includes the features of the previous examples, wherein circulating the liquid drug achieves homogeneous concentration of the drug in the liquid drug solution within the treatment chamber.

An additional example includes the features of the previous examples, wherein circulating the liquid drug solution further comprises continuing to circulate the liquid drug solution until the drug has saturated the target lung tissue area and passed therethrough into the surrounding interstitial space or the proximate lymphatic system of the patient, all of which may act as a conduit or reservoir for the liquid drug solution.

An additional example includes the features of the previous examples, wherein the expandable member is an elastic balloon and predetermined expansion properties thereof comprise a predetermined relationship between inflation volume and diameter.

An additional example includes the features of the previous examples, wherein circulating the liquid drug solution further comprises maintaining a fluid pressure in the treatment chamber below a pre-determined maximum pressure.

An additional example includes a catheter for bilateral local delivery of a drug to target tissue areas of both lungs of a patient, the catheter comprising: an elongate bifurcated flexible shaft; a first expandable member disposed about a first distal branch of the flexible shaft and being transformable between a collapsed delivery configuration and an expanded configuration for sealing against the wall of a first bronchus extending through the first target tissue area to form a treatment chamber defined by the wall of the first bronchus distal of the first expandable member; a first liquid ingress lumen extending from a shaft proximal end to a first liquid ingress port located distal of the first expandable member; and a first liquid egress lumen extending from a shaft proximal end to a first liquid egress port located distal of the first expandable member; wherein the functions of the first ingress and egress ports are reversible such that either port can be a high point of the formed treatment chamber with respect to gravity; a second expandable member disposed about a second distal branch of the flexible shaft and being transformable between a collapsed delivery configuration and an expanded configuration for sealing against the wall of a second bronchus extending through the second target tissue area to form a treatment chamber defined by the wall of the second bronchus distal of the second expandable member; a second liquid ingress lumen extending from a shaft proximal end to a second liquid ingress port located distal of the second expandable member; and a second liquid egress lumen extending from a shaft proximal end to a second liquid egress port located distal of the second expandable member; wherein the functions of the second ingress and egress ports are reversible such that either port can be a high point of the formed treatment chamber with respect to gravity.

An additional example includes the features of the previous examples, and further includes one or more orientation sensors mounted at the first and/or second shaft distal branch and operable to indicate to an operator the orientation of the respective shaft distal region with respect to gravity.

An additional example includes the features of the previous examples, wherein the one or more orientation sensors are accelerometers and/or IMUS adapted to communicate with an electronic console exterior to the patient.

An additional example includes the features of the previous examples, wherein: the first liquid ingress port is located adjacent to the first expandable member and the first liquid egress port is spaced distally of the first liquid egress port; and the second liquid ingress port is located adjacent to the second expandable member and the second liquid egress port is spaced distally of the second liquid egress port.

An additional example includes the features of the previous examples, and further includes one or more navigation cameras disposed adjacent the first and/or the second distal branches.

An additional example includes the features of the previous examples, and further includes at least one port configured for membrane degasification of a liquid drug solution carried by either the first or second liquid ingress or egress lumens.

An additional example includes the features of the previous examples, wherein the at least one membrane degasification port comprises a membrane that is gas-permeable but is not liquid permeable; and wherein the at least one membrane degasification port is one of the first or second liquid ingress or egress ports or the at least one membrane degasification port is located proximal to the first or second expandable member.

An additional example includes the features of the previous examples, and further includes one or more electrodes disposed distally of each of the first and second expandable members.

An additional example includes the features of the previous examples, wherein the electrodes are configured and located to provide an impedance indication when liquid reaches the high point of each of the formed treatment chambers with respect to gravity.

An additional example includes the features of the previous examples, wherein the electrodes are configured and located to provide an impedance indication of a concentration of the drug in the drug solution.

An additional example includes a method for bilateral local delivery of a drug to target tissue areas of both lungs of a patient, the method comprising: inserting a distal region of an elongate bifurcated flexible catheter through a natural orifice such that a first distal catheter branch extends into a first bronchus to a location proximate to a first target tissue area and a second distal catheter branch extends into a second bronchus to a location proximate to a second target tissue area; transforming an expandable member on the first branch from a collapsed delivery configuration to an expanded configuration that sealingly engages a wall of the first bronchus proximal to the first target tissue area to thereby create a first treatment chamber defined by a portion of the first bronchus distal of the first expandable member; transforming an expandable member on the second branch from a collapsed delivery configuration to an expanded configuration that sealingly engages a wall of the second bronchus proximal to the second target tissue area to thereby create a second treatment chamber defined by a portion of the second bronchus distal of the second expandable member; circulating a liquid drug solution containing the drug for the duration of a treatment session through a first closed fluid circuit that comprises the first treatment chamber and two drug-delivery lumens that both extend through the catheter shaft from two respective connecting ports exterior to the patient to two respective chamber ports disposed in the first shaft region distal of the first expandable member; and circulating the liquid drug solution for the duration of the treatment session through a second closed fluid circuit that comprises the second treatment chamber and two drug-delivery lumens that both extend through the catheter shaft from two respective connecting ports exterior to the patient to two respective chamber ports disposed in the second shaft region distal of the second expandable member.

An additional example includes the features of the previous examples, and further includes: purging air from the first and or second treatment chambers before circulating the liquid drug solution, the purging comprising: determining the orientation of the respective distal catheter branch with respect to gravity; repositioning the patient, if necessary, such that one of the chamber ports is located at a high point of the respective treatment chamber with respect to gravity and defining the port so located as a purge port; defining the other chamber port of the respective treatment chamber located below the purge port in the treatment chamber as a fill port; and filling the respective treatment chamber with the liquid drug solution through the fill port while permitting air to exit through the purge port.

An additional example includes the features of the previous examples, and further includes applying negative pressure to the drug-delivery lumen extending from the purge port to enhance purging of air from the treatment chamber.

An additional example includes the features of the previous examples, wherein the purge port is located adjacent to one of the expandable members.

An additional example includes a method for local delivery of a liquid drug solution to a target tissue area surrounding a natural lumen extending through a respiratory tract of a patient, the method comprising: inserting a distal region of an elongate flexible catheter through a natural orifice into a first bronchus of the patient to a location proximate to the target tissue area; inserting an endotracheal tube through the natural orifice into the trachea of the patient; transforming an inflatable cuff on the endotracheal tube from a collapsed delivery configuration to an expanded configuration that sealingly engages the catheter and a tracheal wall at a location above a tracheal carina of the patient; transforming an expandable member on the catheter from a collapsed delivery configuration to an expanded configuration that sealingly engages a wall of the first bronchus proximal to the target tissue area to thereby create a treatment chamber defined by the portion of the first bronchus distal of the expandable member; ventilating a second bronchus opposite the first bronchus through the endotracheal tube; and circulating a liquid drug solution for the duration of a treatment session through a closed fluid circuit that comprises the treatment chamber and two drug-delivery lumens that both extend through a catheter shaft from two respective connecting ports exterior to the patient to two respective chamber ports disposed in the shaft region distal of the expandable member.

An additional example includes the features of the previous examples, wherein transforming an expandable member further comprises adjusting a length of the catheter region distal of the expandable member to correspond with a length of the target tissue area.

An additional example includes the features of the previous examples, wherein circulating the liquid drug solution comprises delivering a known liquid drug concentration with a known tissue permeability of the drug concentration at a selected flow rate for a selected period of time.

An additional example includes the features of the previous examples, wherein circulating the liquid drug solution further comprises pushing a liquid other than the liquid drug solution through the catheter drug-delivery lumen to force the liquid drug solution from the catheter drug-delivery lumen into the treatment chamber.

An additional example includes the features of the previous examples, wherein the two respective chamber ports in the catheter region distal of the expandable member are longitudinally spaced-apart.

An additional example includes the features of the previous examples, and further includes evacuating the treatment chamber before circulating the liquid drug solution.

An additional example includes the features of the previous examples, and further includes degasifying the liquid drug solution in the closed fluid circuit via at least one degasification membrane.

An additional example includes the features of the previous examples, wherein the at least one membrane degasification port is associated with one of the chamber ports, or the at least one membrane degasification port is located proximal to the expandable member.

An additional example includes a catheter for local delivery of a drug to a target tissue area of an internal body organ of a patient, the catheter comprising: an elongate flexible shaft; an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member; a liquid ingress lumen extending from a shaft proximal end to a liquid ingress port located distal to the expandable member; and an egress lumen extending proximally through the flexible shaft from an egress port located distal to the expandable members; wherein the egress port is covered by a membrane that is permeable by gases but not permeable by a liquid containing the drug.

An additional example includes the features of the previous examples, wherein the egress lumen terminates proximally in an exhaust port disposed proximal to both of the expandable member.

An additional example includes the features of the previous examples, wherein the egress port is located adjacent to one of the first and second longitudinally spaced-apart expandable members to facilitate the egress port being located at a high point of the formed treatment chamber with respect to gravity.

An additional example includes the features of the previous examples, and further includes an orientation sensor mounted at the shaft distal region and operable to indicate to an operator the orientation of the shaft distal region with respect to gravity.

An additional example includes the features of the previous examples, wherein the orientation sensor is an accelerometer or an IMU adapted to communicate with an electronic console exterior to the patient.

An additional example includes the features of the previous examples, wherein the liquid ingress port is located adjacent to the first expandable member and the liquid egress port is located adjacent to the second expandable member.

An additional example includes the features of the previous examples, wherein both the first and second expandable members are compliant balloons inflatable to varying diameters, the shaft further having one or more inflation lumens configured for inflating the compliant balloons either simultaneously or independently.

An additional example includes the features of the previous examples, and further includes a navigation camera disposed adjacent the distal region.

An additional example includes the features of the previous examples, and further includes a fiducial marker for referencing the location of the expandable member when the catheter is viewed using a medical imaging system or a navigation system.

An additional example includes the features of the previous examples, wherein the expandable member is configured for forming a closed treatment chamber within a lumen of a gastrointestinal tract, a female genital tract, a urinary tract, or a respiratory tract.

An additional example includes the features of the previous examples, and further includes one or more electrodes disposed distally of the expandable member.

An additional example includes the features of the previous examples, wherein the electrodes are configured and located to provide an impedance indication when liquid reaches the high point of the formed treatment chamber with respect to gravity.

An additional example includes the features of the previous examples, wherein the electrodes are configured and located to provide an impedance indication of a concentration of the drug in the drug solution.

An additional example includes a method for local delivery of a liquid drug solution to a target tissue area of an internal body organ of a patient, the method comprising: inserting a distal region of an elongate flexible catheter shaft through a natural orifice into a natural lumen extending through the target tissue area; transforming an expandable member on the shaft distal region from a collapsed delivery configuration to an expanded configuration in sealing engagement with a wall of the natural lumen to thereby form a treatment chamber defined by the portion of the natural lumen distal of the expandable member; purging air from the treatment chamber, the purging comprising: determining the orientation of the shaft distal region with respect to gravity; repositioning the patient, if necessary, such that a purge port is located at a highpoint of the treatment chamber with respect to gravity; and filling the treatment chamber with the liquid drug solution through a fill port below the purge port while permitting air to exit the treatment chamber through a porous membrane at the purge port until the porous membrane blocks passage of the liquid drug solution through the purge port; and holding the liquid drug solution in the treatment chamber for the duration of a treatment session.

An additional example includes the features of the previous examples, and further includes applying negative pressure to the drug-delivery lumen extending from the purge port to enhance purging of air from the treatment chamber.

An additional example includes the features of the previous examples, wherein the purge port is located adjacent to the expandable member.

An additional example includes the features of the previous examples, wherein the air exiting the treatment chamber through the porous membrane at the purge port is exhausted from the catheter via an exhaust port located proximal to the expandable member.

An additional example includes the features of the previous examples, wherein the air exiting the treatment chamber through the porous membrane at the purge port is exhausted from a portion of the catheter located outside of the patient's body.

An additional example includes the features of the previous examples, and further includes terminating the treatment session and evacuating the treatment chamber of the liquid drug solution after terminating the treatment session.

An additional example includes the features of the previous examples, and further includes measuring a drug concentration in the patient's circulating blood during the treatment session and terminating the treatment session if the measured drug concentration in the blood is equal to or greater than a predetermined minimum threshold amount in the patient's blood.

An additional example includes a non-transitory computer-readable medium having instructions stored thereon that, when executed by at least one processing unit, cause the at least one processing unit to: access image data acquired by non-invasive imaging of a lower respiratory tract of a patient; create, according to the image data, a digital map identifying one or more lung cancer tumors and one or more respiratory airways proximate to the one or more lung cancer tumors; define, according to an analysis of the digital map, one or more tumor treatment zones for permeation of a drug into lung tissue surrounding portions of the one or more respiratory airways, wherein the one or more tumor treatment zones are distal of defined treatment positions of the one or more respiratory airways; and generate a treatment plan according to the one or more tumor treatment zones.

An additional example includes the features of the previous examples, wherein the image data includes computerized tomography (CT) data, magnetic resonance (MR) data, or positron emission tomography (PET) data.

An additional example includes the features of the previous examples, wherein the instructions to define the one or more tumor treatment zones further include at least one of: instructions to identify direct overlap of one or more respiratory airways to a lung cancer tumor, and instructions to assess proximity of one or more respiratory airways to the lung cancer tumor.

An additional example includes the features of the previous examples, wherein the analysis of the digital map includes at least one of a two-dimensional (2D) analysis and a three-dimensional (3D) analysis.

An additional example includes the features of the previous examples, wherein the instructions further cause the computer to: define one or more proposed routes for navigation of a drug-delivery catheter through a respiratory airway system to the defined treatment position in each of the one or more respiratory airways; and include the one or more proposed routes in the treatment plan.

An additional example includes the features of the previous examples, wherein each of the one or more tumor treatment zones is defined to provide drug treatment of an entirety of a respective one of the one or more lung cancer tumors while minimizing drug treatment of non-cancerous tissue.

An additional example includes the features of the previous examples, wherein the instructions to generate the treatment plan further include instructions to generate one or more potential treatment plans for selection by a clinician.

An additional example includes the features of the previous examples, wherein the instructions to define the tumor treatment zones further include instructions to: access clinician-selectable features as inputs for generating the treatment plan, the inputs including at least one of: a) a drug delivery distance from a tumor edge, b) a maximum number of defined treatment positions in a single treatment plan, and c) a minimum diameter of a respiratory airway for placement of a drug delivery catheter; and use the inputs to define the tumor treatment zones.

An additional example includes the features of the previous examples, wherein the instructions further include instructions to guide manual or robotic placement of a drug delivery catheter to the defined treatment position in each of the one or more respiratory airways.

An additional example includes the features of the previous examples, wherein the instructions to define the one or more tumor treatment zones further include instructions to define two tumor treatment zones surrounding portions of two different respiratory airways, the two tumor treatment zones abutting each other to provide drug treatment of at least one tumor.

An additional example includes a system comprising: at least one memory unit; at least one processing unit programmed according to instructions on the at least one memory unit to configure the at least one processing unit to: access image data acquired by non-invasive imaging of a lower respiratory tract of a patient; create, according to the image data, a digital map identifying one or more lung cancer tumors and one or more respiratory airways proximate to the one or more lung cancer tumors; define, according to an analysis of the digital map, one or more tumor treatment zones for permeation of a drug into lung tissue surrounding portions of the one or more respiratory airways, wherein the one or more tumor treatment zones are distal of defined treatment positions of the one or more respiratory airways; and generate a treatment plan according to the one or more tumor treatment zones.

An additional example includes the features of the previous examples, wherein the image data includes computerized tomography (CT) data, magnetic resonance (MR) data, or positron emission tomography (PET) data.

An additional example includes the features of the previous examples, wherein the at least one processing unit is further configured to define the one or more tumor treatment zones by at least one of: identifying direct overlap of one or more respiratory airways to a lung cancer tumor and assessing proximity of one or more respiratory airways to the lung cancer tumor.

An additional example includes the features of the previous examples, wherein the analysis of the digital map includes at least one of a two-dimensional (2D) analysis and a three-dimensional (3D) analysis.

An additional example includes the features of the previous examples, the at least one processing unit is further configured to define one or more proposed routes for navigation of a drug-delivery catheter through a respiratory airway system to the defined treatment position in each of the one or more respiratory airways; and include the one or more proposed routes in the treatment plan.

An additional example includes the features of the previous examples, wherein the at least one processing unit is further caused to define each of the one or more tumor treatment zones to provide drug treatment of an entirety of a respective one of the one or more cancer tumors while minimizing drug treatment of non-cancerous tissue.

An additional example includes the features of the previous examples, wherein the at least one processing unit is further configured to generate one or more potential treatment plans for selection by a clinician to generate the treatment plan.

An additional example includes the features of the previous examples, wherein the at least one processing unit is further configured to: access clinician-selectable features as inputs for defining the tumor treatment zones, the inputs including at least one of: a) drug delivery distance from tumor edge, b) maximum number of defined treatment position in a single treatment plan, and c) minimum diameter of airway for placement of a drug delivery catheter, and use the inputs to define the tumor treatment zones.

An additional example includes the features of the previous examples, wherein the at least one processing unit is further configured to guide manual or robotic placement of a drug delivery catheter to the defined treatment position in each of the one or more respiratory airways.

An additional example includes the features of the previous examples, wherein the at least one processing unit is further configured to define the one or more tumor treatment zones by defining two tumor treatment zones surrounding portions of two different respiratory airways, the two tumor treatment zones abutting each other to provide drug treatment of at least one tumor.

An additional example includes a computer-implemented method for generating a tumor treatment the method being implemented by at least one processing unit programmed with computer program instructions that, when executed, cause the at least one processing unit to perform the method, the method comprising: accessing image data acquired by non-invasive imaging of a lower respiratory tract of a patient; creating a digital map identifying one or more lung cancer tumors and one or more respiratory airways proximate to the one or more lung cancer tumors according to the image data; defining, according to an analysis of the digital map, one or more tumor treatment zones for permeation of a drug into lung tissue surrounding portions of one or more respiratory airways, wherein the one or more tumor treatment zones are distal of defined treatment positions of the one or more respiratory airways; and generating a treatment plan according to the one or more tumor treatment zones.

An additional example includes the features of the previous examples, wherein the image data includes computerized tomography (CT) data, magnetic resonance (MR) data, or positron emission tomography (PET) data.

An additional example includes the features of the previous examples, wherein defining the one or more tumor treatment zones further includes at least one of: identifying direct overlap of the one or more respiratory airways to a lung cancer tumor and assessing proximity of the one or more respiratory airways to the lung cancer tumor.

An additional example includes the features of the previous examples, wherein the analysis of the digital map includes at least one of a two-dimensional (2D) analysis and a three-dimensional (3D) analysis.

An additional example includes the features of the previous examples, and further includes defining one or more proposed routes for navigation of a drug-delivery catheter through a respiratory airway system to the defined treatment position in each of the one or more respiratory airways; and including the one or more proposed routes in the treatment plan.

An additional example includes the features of the previous examples, and further includes defining the one or more tumor treatment zones to provide drug treatment of an entirety of a respective one of the one or more lung cancer tumors while minimizing drug treatment of non-cancerous tissue.

An additional example includes the features of the previous examples, wherein generating the treatment plan further include generating one or more potential treatment plans for selection by a clinician.

An additional example includes the features of the previous examples, wherein defining the tumor treatment zones further includes: accessing clinician-selectable features as inputs for defining the tumor treatment zones, the inputs including at least one of: a) a drug delivery distance from a tumor edge, b) a maximum number of defined treatment position in a single treatment plan, and c) a minimum diameter of a respiratory airway for placement of a drug delivery catheter, and using the inputs to define the tumor treatment zones generate the treatment plan.

An additional example includes the features of the previous examples, and further includes guiding manual or robotic placement of a drug delivery catheter to the defined treatment position in each of the one or more respiratory airways.

An additional example includes the features of the previous examples, wherein defining tumor treatment zones further includes defining two tumor treatment zones surrounding portions of two respiratory different airways, the two tumor treatment zones abutting each other to provide drug treatment of at least one tumor.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described exemplary embodiments but should be defined only in accordance with the appended claims and their equivalents. It will also be apparent that all hollow organs are eligible for both single and multiple balloon configurations of the devices, systems and methods described herein. It will also be understood that each feature of each embodiment discussed herein, and of each reference cited herein, can be used in combination with the features of any other embodiment.

What is claimed is:

1. A system for providing tumor treatment within a respiratory tract, the system comprising:
   a drug-delivery catheter;
   at least one memory unit;
   at least one processing unit programmed according to instructions on the at least one memory unit to configure the at least one processing unit to:
      access image data acquired by non-invasive imaging of a lower respiratory tract of a patient;
      create, according to the image data, a digital map identifying one or more lung cancer tumors and one or more respiratory airways;

select one or more identified respiratory airways of the one or more respiratory airways that are proximate to or overlapping the one or more lung cancer tumors;

identify, according to an analysis of the digital map, defined treatment positions in the one or more respiratory airways for delivery of a chemotherapeutic drug solution to one or more treatment chambers defined by the drug-delivery catheter within the one or more respiratory airways, determine one or more tumor treatment zones for permeation of the chemotherapeutic drug solution into lung tissue surrounding the treatment chamber when the chemotherapeutic drug solution is delivered to the one or more treatment zones, wherein the one or more tumor treatment zones are defined as the lung tissue surrounding the entire portion of the one or more distal respiratory airways distal of the defined treatment positions in the one or more respiratory airways;

compare the one or more tumor treatment zones to the one or more lung cancer tumors to determine whether the one or more treatment zones exceed the margins of the one or more lung cancer tumors;

backtrack the defined treatment positions to successively more proximal positions within the one or more respiratory airways to include additional airways and increase the size of the one or more treatment zones until the one or more treatment zones associated with the defined treatment positions exceed the margins the one or more lung cancer tumors; and generate a treatment plan according to the defined treatment positions, wherein the drug-delivery catheter is configured to:

be delivered to the defined treatment positions;

create the one or more treatment chambers including the entire portion of the one more distal respiratory airways distal of the defined treatment positions; and circulate the chemotherapeutic drug solution within the one or more treatment chambers.

2. The system of claim 1, wherein the image data includes computerized tomography (CT) data, magnetic resonance (MR) data, or positron emission tomography (PET) data.

3. The system of claim 1, wherein the at least one processing unit is further configured to define the one or more tumor treatment zones by at least one of:

identifying direct overlap of one or more respiratory airways to a lung cancer tumor, and assessing proximity of one or more respiratory airways to the lung cancer tumor.

4. The system of claim 1, wherein the analysis of the digital map includes at least one of a two-dimensional (2D) analysis and a three-dimensional (3D) analysis.

5. The system of claim 1, the at least one processing unit is further configured to define one or more proposed routes for navigation of the drug-delivery catheter through a respiratory airway system to the defined treatment position in each of the one or more respiratory airways; and include the one or more proposed routes in the treatment plan.

6. The system of claim 1, wherein the at least one processing unit is further configured to:

access clinician-selectable features as inputs for defining the one or more tumor treatment zones, the inputs including at least one of:

a) drug delivery distance from tumor edge, b) maximum number of defined treatment position in a single treatment plan, and c) minimum diameter of airway for placement of a drug delivery catheter, and use the inputs to define the one or more tumor treatment zones.

7. The system of claim 1, wherein the at least one processing unit is further configured to define the one or more tumor treatment zones by defining two tumor treatment zones surrounding portions of two different respiratory airways, the two tumor treatment zones abutting each other to provide drug treatment of at least one tumor.

8. A method for providing tumor treatment plan within a respiratory tract using a drug-delivery catheter configured to create a treatment chamber distal to a treatment position in a respiratory airway and circulate chemotherapeutic drug solution within the treatment chamber, the method comprising:

accessing, by at least one processing unit programmed with computer program instructions, image data acquired by non-invasive imaging of a lower respiratory tract of a patient;

creating, by the at least one processing unit according to the image data, a digital map identifying one or more lung cancer tumors and one or more respiratory airways;

selecting, by the at least one processing unit, one or more identified respiratory airways of the one or more respiratory airways that are proximate to or overlapping the one or more lung cancer tumors;

identifying, by the at least one processing unit, according to an analysis of the digital map, defined treatment positions in the one or more respiratory airways for delivery of the chemotherapeutic drug solution to one or more treatment chambers defined by the drug-delivery catheter within the one or more respiratory airways, wherein the one or more treatment chambers are defined as the respective respiratory tracts distal of the defined treatment positions, determining, by the at least one processing unit, one or more tumor treatment zones for permeation of the chemotherapeutic drug solution into lung tissue surrounding the treatment chamber when the chemotherapeutic drug solution is delivered to the one or more treatment zones, wherein the one or more tumor treatment zones are defined as the lung tissue surrounding the entire portion of the one or more distal respiratory airways distal of the defined treatment positions in the one or more respiratory airways;

comparing, by the at least one processing unit the one or more tumor treatment zones to the one or more lung cancer tumors to determine whether the one or more treatment zones exceed the margins of the one or more lung cancer tumors;

backtracking, by the at least one processing unit, the defined treatment positions to successively more proximal positions within the one or more respiratory airways to include additional airways and increase the size of the one or more treatment zones until the one or more treatment zones associated with the defined treatment positions exceed the margins the one or more lung cancer tumors;

generating, by the at least one processing unit, a treatment plan according to the defined treatment positions, and carrying out the treatment plan via the drug-delivery catheter by delivering the chemotherapeutic drug solution at the defined treatment positions.

9. The method of claim 8, wherein the image data includes computerized tomography (CT) data, magnetic resonance (MR) data, or positron emission tomography (PET) data.

10. The method of claim 8, wherein defining the one or more tumor treatment zones further includes at least one of:

identifying direct overlap of the one or more respiratory airways to a lung cancer tumor, and assessing proximity of the one or more respiratory airways to the lung cancer tumor.

11. The method of claim 8, wherein the analysis of the digital map includes at least one of a two-dimensional (2D) analysis and a three-dimensional (3D) analysis.

12. The method of claim 8, further comprising:

defining one or more proposed routes for navigation of the drug-delivery catheter through a respiratory airway system to the defined treatment position in each of the one or more respiratory airways; and including the one or more proposed routes in the treatment plan.

13. The method of claim 8, wherein defining the one or more tumor treatment zones further includes:

accessing clinician-selectable features as inputs for defining the one or more tumor treatment zones, the inputs including at least one of:

a) a drug delivery distance from a tumor edge, b) a maximum number of defined treatment position in a single treatment plan, and c) a minimum diameter of a respiratory airway for placement of a drug delivery catheter, and using the inputs to define the one or more tumor treatment zones.

\* \* \* \* \*